(12) United States Patent
Gawin et al.

(10) Patent No.: US 11,999,754 B2
(45) Date of Patent: Jun. 4, 2024

(54) RUTHENIUM COMPLEXES AND THEIR USE IN OLEFIN METATHESIS REACTIONS

(71) Applicant: APEIRON SYNTHESIS S.A., Wroclaw (PL)

(72) Inventors: Rafal Gawin, Warsaw (PL); Patryk Krajczy, Glogowek (PL); Anna Gawin, Warsaw (PL); Krzysztof Skowerski, Jablonowo Pomorskie (PL)

(73) Assignee: APEIRON SYNTHESIS S.A., Wroclaw (PL)

( * ) Notice: Subject to any disclaimer, the term of this patent is extended or adjusted under 35 U.S.C. 154(b) by 759 days.

(21) Appl. No.: 17/048,092

(22) PCT Filed: Apr. 16, 2019

(86) PCT No.: PCT/IB2019/053138
§ 371 (c)(1),
(2) Date: Oct. 15, 2020

(87) PCT Pub. No.: WO2019/202509
PCT Pub. Date: Oct. 24, 2019

(65) Prior Publication Data
US 2021/0101922 A1    Apr. 8, 2021

(30) Foreign Application Priority Data
Apr. 16, 2018 (PL) .......................... 425237

(51) Int. Cl.
*C07F 15/00* (2006.01)
*B01J 31/18* (2006.01)
*C07C 6/04* (2006.01)

(52) U.S. Cl.
CPC ....... *C07F 15/0046* (2013.01); *B01J 31/1825* (2013.01); *C07C 6/04* (2013.01); *C07C 2531/22* (2013.01)

(58) Field of Classification Search
CPC ..................................................... C07F 15/00
USPC ............................................................ 548/103
See application file for complete search history.

(56) References Cited

FOREIGN PATENT DOCUMENTS

| WO | 2011/056881 A2 | 5/2011 |
| WO | 2017/185324 A1 | 11/2017 |
| WO | 2017185324 | * 11/2017 |

* cited by examiner

*Primary Examiner* — Niloofar Rahmani
(74) *Attorney, Agent, or Firm* — Dickinson Wright PLLC; Andrew D. Dorisio

(57) ABSTRACT

The invention relates to a ruthenium complex of formula (1), (1) wherein all variables have a meaning as defined in the specification to be used as a (pre)catalyst in the olefin metathesis reaction, ring metathesis reaction (RCM), homo-metathesis (self-CM), cross-metathesis including ethanolysis (CM).

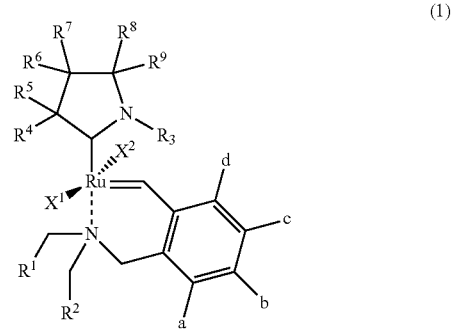

(1)

15 Claims, No Drawings

RUTHENIUM COMPLEXES AND THEIR USE IN OLEFIN METATHESIS REACTIONS

The invention relates to novel N-chelating ruthenium complexes useful as catalysts and/or (pre)catalysts of olefin metathesis reaction and their use in olefin metathesis reactions. This invention is applicable in the field of broadly understood organic synthesis.

In the last years, a great progress was made in the use of olefin metathesis in organic synthesis [R. H. Grubbs (Editor), A. G. Wenzel (Editor), D. J. O'Leary (Editor), E. Khosravi (Editor), *Handbook of Olefin Metathesis*, 2nd edition, 3 volumes 2015, John Wiley & Sons, Inc., 1608 pages]. Many catalysts are known from prior art that have both high activity in various types of metathesis reactions and high tolerance to functional groups. The combination of these features makes metathesis catalysts very important in modern organic synthesis and industry. The (pre)catalysts that are most widely described in literature are Grubbs, Hoveyda, and indenylidene complexes, and recently Bertrand type catalysts having a carbene cycloalkylamine ligand (CAAC)[Grubbs et al. *Chem. Rev.* 2010, 110, 1746-1787; Nolan et al. *Chem. Commun.* 2014, 50, 10355-10375]. In other cases, most structures of olefin metathesis catalysts derive from the ruthenium complexes listed above.

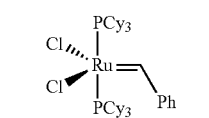

Gru-I

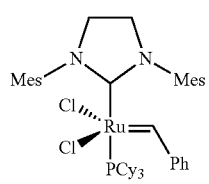

Gru-II

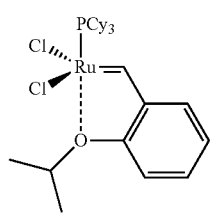

Hov-I

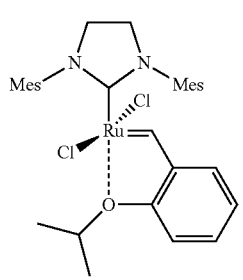

Hov-II

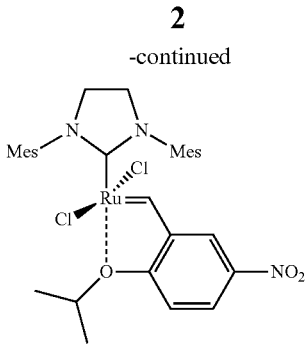

Gre-II

There are many examples of industrial applications of ruthenium complexes wherein the use of fast initiating (pre)catalysts is preferable. A representative example is the use of the Gre-II catalyst in a macrocyclization reaction [Farina, V., Shu, C., Zeng, X, Wei, X, Han, Z., Yee, N. K., Senanayake, C. H., *Org. Process Res. Dev.,* 2009, 13, 250-254]. The use of Gre-II in this process allowed for significantly reducing the amount of the catalyst used and for reducing the solvent volume compared to the process conditions where Hov-I catalyst was used. Increasing the rate of catalyst Gre-II initiation was achieved by inserting the electron-acceptor nitro group [WO 2004/035596A1]. The nitro substituent causes a decrease in electron density on the ether oxygen atom. As a result, the Ru—O interaction is diminished, which makes the Gre-II complex a fast initiator of the metathesis reaction.

Many catalysts are reported in prior art, whose modifications were designed to affect the effect of (pre)catalysts by changing electron density on the heteroatom chelating to ruthenium. Among these modifications, benzylidene ligands having such atoms as nitrogen, sulphur, selenium and phosphorus, which coordinate to ruthenium, have been reported [Diesendruck, C. E., Tzur, E., Ben-Asuly, A., Goldberg, I., Straub, B. F., Lemcoff, N. G., *Inorg. Chem.* 2009, 48, 10819-10825].

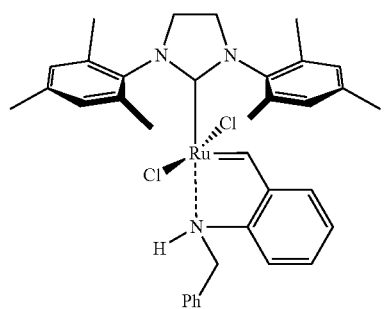

4

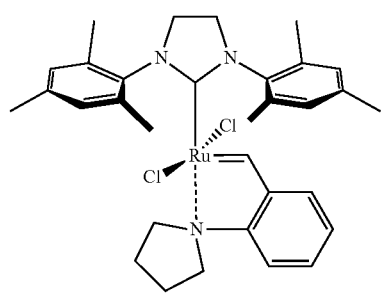

5

The most widely reported modifications include those where the chelating oxygen atom is replaced by a nitrogen atom. Slugovc described complexes having a Schiff base in the benzylidene ligand [Slugovc, C., Butscher, D., Stelzer, F., Mereiter, K., *Organometallics* 2005, 24, 2255-2258]. Grela presented the structure of the complex having the N-pyridine ligand [Szadkowska, A., Gstrein, X., Burtscher, D., Jarzembska, K., Woźniak, K., Slugovc, C., Grela, K., *Organometallics* 2010, 29, 117-124] and a number of complexes having a secondary amine in the benzylidene ligand (4) [Żukowska, K., Szadkowska, A., Pazio, A., Woźniak, K., Grela, K., *Organometallics* 2012, 31, 462-469]. Another example is a complex having a ligand with a chelating nitrogen atom, whose alkyl substituents together with the nitrogen atom form a pyrolydine ring (5) [Tzur, E., Szadkowska, A., Ben-Asuly, A., Makal, A., Goldberg, I., Woźniak, K., Grela, K., Lemcoff, N. G., *Chem. Eur. J.* 2010, 16, 8726-8737]. The (pre)catalysts listed above are examples of N-chelating "dormant" complexes, whose activation requires an increase in temperature or an addition of an acid, e.g. Lewis acid. Their dormancy is caused by the high electron density at the nitrogen atom, which is associated with a potent Ru—N interaction and slow initiation.

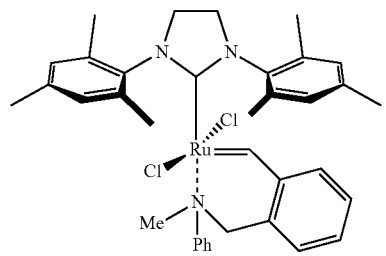

6

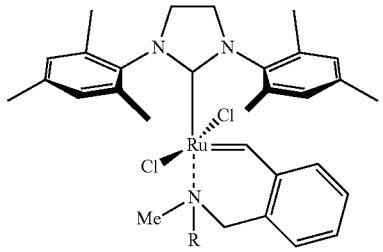

7a-f

7a, R = Me
7b, R = Et
7c, R = CH$_2$CH$_2$OCH$_3$

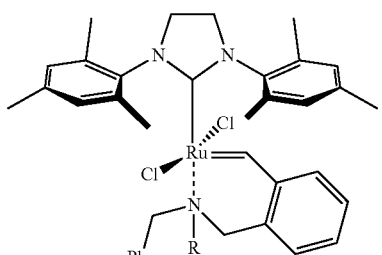

8a-c

8a, R = CH$_2$Ph
8b, R = Me
8c, R = Et

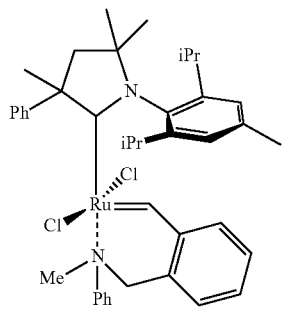

9

"Dormant" N-heterocyclic (pre)catalysts that have benzylidene ligands containing, in the ortho position, the moiety: —CH$_2$NR$_2$ or —CH$_2$NRR' (6-8) are also known from prior art. This moiety forms a six-member ring chelating the ruthenium atom. The properties ("dormancy") of these complexes can also be explained by the high electron density at the nitrogen atom, which causes a potent Ru—N effect. These catalysts are described in patent applications WO 2017/185324 A1 (6), WO 2015/126279 A1 (7, 8) and patent document RU 2462308 C1 (7, 8). Catalysts of this type are used as ROMP reaction initiators.

Moreover, a case of introducing cycloalkylamine carbene 9 (CAAC) in place of N-heterocyclic carbene (WO 2017/185324 A1) was reported. This catalyst has been tested in the ethenolysis reaction and it has been noted that despite this modification, it requires chemical activation (addition of HSiCl$_3$).

Catalyst initiation rate depends e.g. on the strength of the Ru—N bond (or Ru-another chelating heteroatom) in the benzylidene ligand. In case of a potent Ru—N interaction, the catalyst is slowly initiating ("dormant", requires thermal or chemical activation) and is usually used in ROMP polymerisation reactions. In catalysts 6-9, the nitrogen atom (in the benzylidene ligand) strongly interacts with ruthenium.

Electron density at nitrogen atom is increased by alkyl substituents. Electron density can be correlated with the change in alkalinity in a number of differently substituted amines [Hoefnagel, A. J., Hoefnalgel, M. A., Wepster, B. M., *J. Org. Chem.* 1981, 46, 4209-4211].

The ready availability of a catalyst is essential for industrial applicability. This is associated with the smooth synthesis of its precursor (ligand) on a large scale. Despite the high activity of Gre-II (pre)catalyst, the synthesis of its precursor—benzylidene ligand—necessitates multiple steps and involves a number of technological issues that are difficult to solve on a large scale. As regards the precursor of the Gre-II complex, some steps require strictly defined reaction conditions (temperature of 200° C.), while the yield of intermediates is low. For the purposes of industrial applicability, it is desirable for a class of catalysts to be developed with a wide range of applications, which is characterised by both simple—technologically speaking—synthesis and synthesis of required precursors on an industrial scale.

Thus, the aim of this invention was to develop a novel class of catalysts with a wide range of applications, readily synthesisable and also using readily synthesisable precursors.

Surprisingly, it was found that (pre)catalysts—ruthenium complexes according to the invention represented by formula 1 have high activity in olefin metathesis reactions at relatively low temperatures and without additional chemical activation.

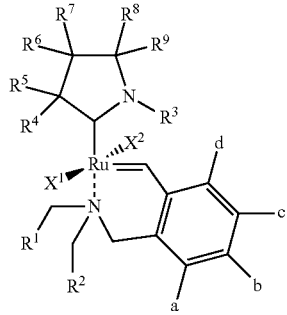

Prior art does not suggest that a catalyst with the general formula 1 (having the CAAC ligand), which has at least one $R^1$ or $R^2$ aryl substituent in the benzene moiety will show high activity. Introduction of an aryl group ($R^1$ or $R^2$) due to the isolating methylene group (between $R^1$ or $R^2$ and the nitrogen atom) does not significantly reduce the electron density at the nitrogen atom (as is the case with the "dormant" (pre)catalysts (8) known from prior art), which should therefore result in a low activity of (pre)catalysts 1.

In addition, intermediates 3, derivatives of 2-vinylbenzylamine, which are used in the synthesis of catalysts with the formula 1, are obtained in a series of simple reactions with high yields [Examples XI-XVIII]. This enables their easy synthesis on an industrial scale, which directly translates into the availability of complexes represented by the formula 1 on an industrial scale.

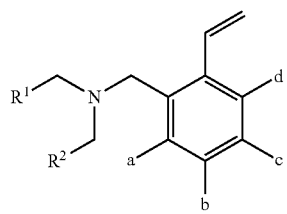

Complexes with the formula 1 according to the invention are applicable in a wide range of reactions. Ring metathesis (RCM), cross-metathesis (CM), and homometathesis (self-CM) reactions can be performed with good results. (Pre)catalysts with the general formula 1 in metathesis reactions have a much higher activity compared to complexes having alkyl substituents at the nitrogen atom. Moreover, complexes with formula 1 have high stability in solutions and solids.

Therefore, the invention relates to new ruthenium complexes represented by the formula 1:

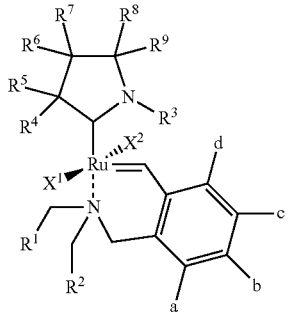

wherein:
$X^1$, $X^2$ are each independently an anionic ligand selected from such as halogen atom, —OR, —SR, —C(C=O)R, where R is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, optionally $C_1$-$C_{12}$ perhalogenalkyl, optionally $C_1$-$C_{12}$ alkoxy, optionally a halogen atom;

$R^1$—is a hydrogen atom or $C_5$-$C_{24}$ aryl, $C_1$-$C_{25}$ alkyl, $C_5$-$C_{25}$ heteroaryl, $C_7$-$C_{24}$ aralkyl, which are optionally substituted by at least one $C_1$-$C_{12}$ alkyl, optionally $C_1$-$C_{12}$ perhalogenalkyl, optionally $C_1$-$C_{12}$ alkoxy, optionally a halogen atom, wherein the alkyl groups may be interconnected to form a ring;

$R^2$—is $C_5$-$C_{24}$ aryl, $C_5$-$C_{25}$ heteroaryl, $C_7$-$C_{24}$ aralkyl, which are optionally substituted by at least one $C_1$-$C_{12}$ alkyl, optionally $C_1$-$C_{12}$ perhalogenalkyl, optionally $C_1$-$C_{12}$ alkoxy, optionally a halogen atom, wherein the alkyl groups may be interconnected to form a ring;

$R^3$ is $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_2$-$C_{12}$ alkoxy or a halogen atom;

$R^4$, $R^5$, $R^6$, $R^7$, $R^8$, $R^9$ are each independently a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_1$-$C_{12}$ alkoxy or a halogen atom, and the $R^4$ and $R^5$ and/or $R^8$ and $R^9$ groups may optionally be interconnected to form a cyclic system $C_4$-$C_{10}$;

a, b, c, d—are each independently a hydrogen atom, a halogen atom, $C_1$-$C_{25}$ alkyl, $C_1$-$C_{25}$ perfluoroalkyl, $C_3$-$C_7$ cycloalkyl, $C_1$-$C_{25}$ alkoxy, $C_5$-$C_{24}$ aryl, $C_7$-$C_{24}$ aralkyl, $C_5$-$C_{25}$ heteroaryl, 3-12-membered heterocycle, wherein the alkyl groups may be interconnected to form a ring; also, each of them can be independently an ether (—OR'), thioether (—SR'), nitro (—$NO_2$), cyano (—CN), amide (—CONR'R"), carboxy and ester (—COOR'), sulfo (—$SO_2$R'), sulfonamide (—$SO_2$NR'R"), formyl and ketone (—COR') group, in which groups R' and R" are each independently $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl;

Compounds with the general formula 1 are preferable, wherein:
$X^1$ and $X^2$ are halogen atoms;
$R^3$ is aryl, which is optionally substituted by at least one $C_1$-$C_{12}$ alkyl, $C_1$-$C_{12}$ perhalogenalkyl, $C_2$-$C_{12}$ alkoxy or a halogen atom;
$R^4$, $R^5$, $R^8$, $R^9$ are each independently a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_1$-$C_{12}$ alkoxy or a halogen atom, and the $R^4$ and $R^5$ and/or $R^8$ and $R^9$ groups may optionally be interconnected to form a cyclic system $C_4$-$C_{10}$;

$R^6$, $R^7$ are hydrogen atoms;

a, b, c, d—are each independently a halogen atom, an ether (—OR'), thioether (—SR'), nitro (—NO$_2$), cyano (—CN), amide (—CONR'R"), carboxy and ester (—COOR'), sulfo (—SO$_2$R'), sulfonamide (—SO$_2$NR'R"), formyl and ketone (—COR') group, in which groups R' and R" are each independently $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl;

Compounds with the general formula 1 are preferable, wherein:

$X^1$ and $X^2$ are halogen atoms;

$R^3$ is aryl, which is optionally substituted by at least one $C_1$-$C_{12}$ alkyl, $C_1$-$C_{12}$ perhalogenalkyl, $C_2$-$C_{12}$ alkoxy or a halogen atom;

$R^4$, $R^5$, $R^8$, $R^9$ are each independently a hydrogen atom, $C_1$-$C_{12}$ alkyl, $C_3$-$C_{12}$ cycloalkyl, $C_5$-$C_{20}$ aryl, which is optionally substituted by at least one $C_1$-$C_{12}$ alkyl, and the $R^4$ and $R^5$ and/or $R^8$ and $R^9$ groups may optionally be interconnected to form a cyclic system $C_4$-$C_{10}$;

$R^6$, $R^7$ are hydrogen atoms;

a, b, c, d—are each independently a halogen atom, an ether (—OR'), nitro (—NO$_2$), amide (—CONR'R"), ester (—COOR'), sulfo (—SO$_2$R'), sulfonamide (—SO$_2$NR'R") group, in which groups R' and R" are each independently $C_1$-$C_{25}$ alkyl, $C_5$-$C_{24}$ aryl;

Compounds with the general formula 1 are preferable, wherein:

$X^1$ and $X^2$ are chlorine atoms;

$R^3$ is aryl, which is optionally substituted by at least one $C_1$-$C_{12}$ alkyl;

$R^4$, $R^5$ are each independently $C_1$-$C_{12}$ alkyl, $C_5$-$C_{20}$ aryl, which is optionally substituted by at least one $C_1$-$C_{12}$ alkyl, and the $R^4$ and $R^5$ groups may optionally be interconnected to form a cyclic system $C_4$-$C_{10}$;

$R^6$, $R^7$ are hydrogen atoms;

$R^8$, $R^9$ are each independently $C_1$-$C_{12}$ alkyl, a, b, c, d—are each independently a hydrogen atom or an ether (—OR') group, in which group R' denotes as follows: $C_1$-$C_{25}$ alkyl;

Compounds with the general formula 1 are preferable, wherein:

$X^1$ and $X^2$ are chlorine atoms;

$R^3$ is aryl, which is optionally substituted by at least one $C_1$-$C_{12}$ alkyl;

$R^4$, $R^5$ are each independently $C_1$-$C_{12}$ alkyl, $C_5$-$C_{20}$ aryl, and the $R^4$ and $R^5$ groups may optionally be interconnected to form a cyclic system $C_4$-$C_{10}$;

$R^6$, $R^7$ are hydrogen atoms;

$R^8$, $R^9$ are each independently methyl groups, a, b, c, d—are each independently a hydrogen atom or a metoxy (—OMe) group;

Preferably, ruthenium complexes according to the invention with a general formula 1 have a structure represented by a structural formula selected from the 1a-1j formulas;

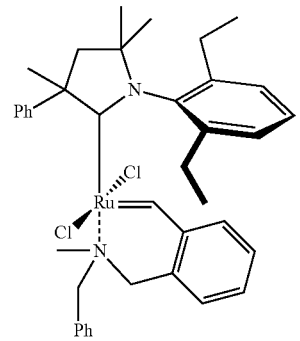

1a

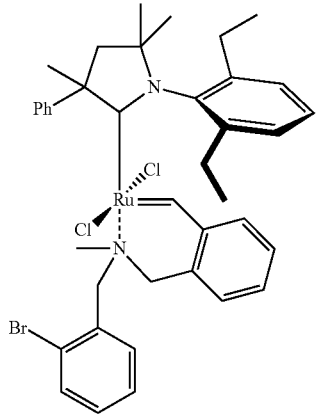

1b

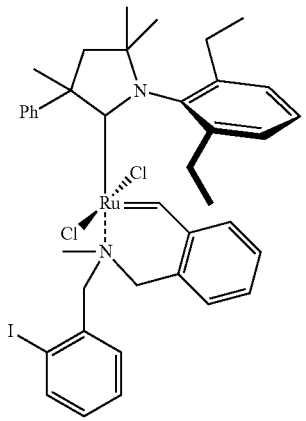

1c

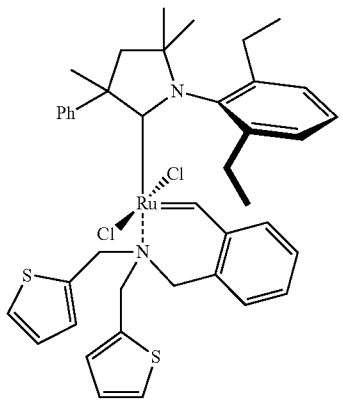

1d

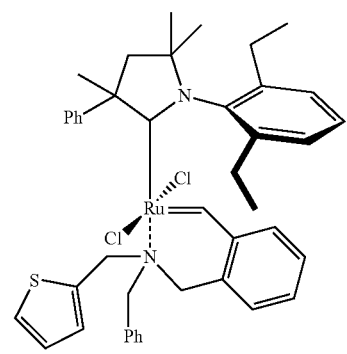

1e

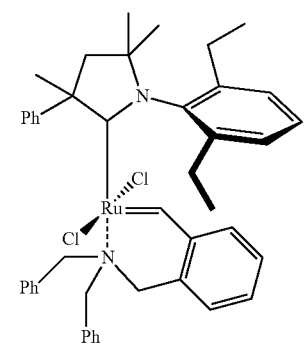

1f

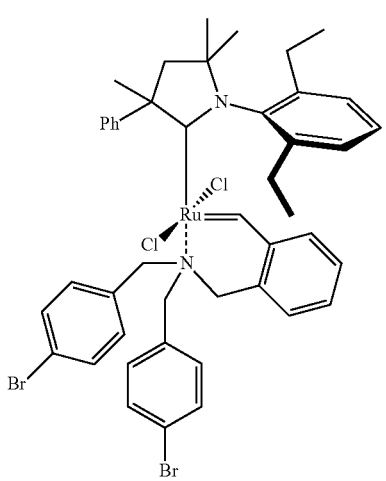

1g

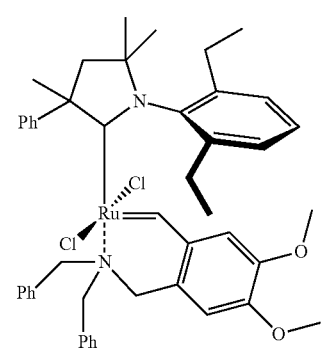

1h

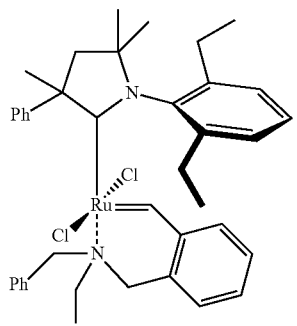

1i

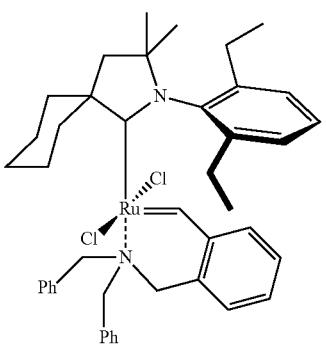

1j

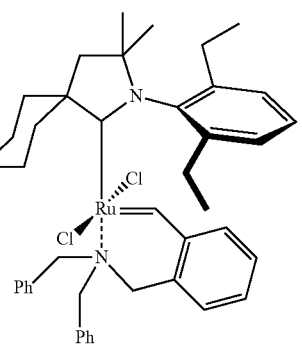

The invention also relates to the use of ruthenium complexes according to the invention as metathesis reaction (pre)catalysts. (Pre)catalysts according to the invention are widely used in organic synthesis. The synthesis of compounds that contain the C═C bond and other functional groups, using complexes 1, yields very good results. The new (pre)catalysts described here were found to be more effective than the state-of-the-art catalysts: both N-chelating complexes with N-heterocyclic carbide and CAAC carbide (Example XIX-XXI). The use of complexes with the general formula 1 allows for significantly reducing the amount of (pre)catalyst used, reducing the concentration of the reaction mixture, and to conducting a metathesis reaction without the use of a solvent. The characteristics listed above are desirable from the point of view of industrial applicability of ruthenium complexes as metathesis reaction (pre)catalysts.

Preferably, the catalysed metathesis reaction includes a reaction chosen from those such as ring metathesis reaction (RCM), homomethathesis (self-CM), cross metathesis, including ethenolysis (CM).

Preferably, the reaction is conducted in an organic solvent such as toluene, benzene, mesitylene, dichloromethane, ethyl acetate, methyl acetate, tertbutyl methyl ether, cyclopentyl methyl ether, or with no solvent.

Preferably, the reaction is conducted at a temperature from 0 to 150° C.

Preferably, the reaction is conducted at a temperature from 40 to 120° C.

Preferably, the reaction is conducted over 1 minute to 24 hours.

Preferably, compound 1 is used in an amount of no more than 0.1 mol %.

Preferably, compound 1 is added to the reaction mixture as a solid and/or as a solution in an organic solvent.

The terms used in the present description shall be understood as follows. Non-defined terms herein have the meaning given and understood by a person skilled in the art in the light of the best knowledge held, of the present disclosure, and of the context of the specification of the patent application. Unless indicated otherwise, the following conventional chemistry terms are used in the present specification that have the meanings indicated in the definitions below.

The term "halogen atom" used herein refers to an element selected from F, Cl, Br, I.

The term "carbene" refers to a particle containing a neutral carbon atom with a valence number of two and having two unpaired valence electrons. The term "carbene" also includes carbene analogs in which the carbon atom is substituted by another chemical element such as boron, silicon, germanium, tin, lead, nitrogen, phosphorus, sulphur, selenium and tellurium.

The term "alkyl" refers to a saturated, linear or branched hydrocarbon substituent having the indicated number of carbon atoms. Examples of alkyl substituents include -methyl, -ethyl, -n-propyl, -n-butyl, -n-pentyl, -n-hexyl, -n-heptyl, -n-octyl, -n-nonyl, and -n-decyl. Representative branched-(C1-C10)alkyls include -isopropyl, -sec-butyl, -isobutyl, -tert-butyl, -isopentyl, -neopentyl, -1-methylobutyl, -2-methylobutyl, -3-methylobutyl, -1,1-dimethylopropyl, -1,2-dimethylopropyl, -1-methylopentyl, -2-methylopentyl, -3-methylopentyl, -4-methylopentyl, -1-ethylobutyl, -2-ethylobutyl, -3-ethylobutyl, -1,1-dimethylobutyl, -1,2-dimethylobutyl, -1,3-dimethylobutyl, -2,2-dimethylobutyl, -2,3-dimethylobutyl, -3,3-dimethylobutyl, -1-methylohexyl, -2-methylohexyl, -3-methylohexyl, -4-methylohexyl, -5-methylohexyl, -1,2-dimethylopentyl, -1,3-dimethylopentyl, -1,2-dimethylohexyl, -1,3-dimethylohexyl, -3,3-dimethylohexyl, -1,2-dimethyloheptyl, -1,3-dimethyloheptyl, and -3,3-dimethyloheptyl and the like.

The term "alkoxy" refers to an alkyl substituent as defined above bound by an oxygen atom.

The term "berfluoroalkyl" refers to an alkyl group as defined above in which all the hydrogen atoms have been substituted by the same or different halogen atoms.

The term "cycloalkyl" refers to a saturated mono- or polycyclic hydrocarbon substituent having the indicated number of carbon atoms. Examples of cycloalkyl substituents include -cyclopropyl, -cyclobutyl, -cyclopentyl, -cyclohexyl, -cycloheptyl, -cyclooctyl, -cyclononyl, -cyclodecyl and the like.

The term "alkenyl" refers to a saturated, linear or branched non-cyclic hydrocarbon substituent of the indicated number of carbon atoms and containing at least one double carbon-carbon bond. Examples of alkenyl substituents include -vinyl, -allyl, -1-butenyl, -2-butenyl, -isobutylenyl, -1-pentenyl, -2-pentenyl, -3-methylo-1-butenyl, -2-methylo-2-butenyl, -2,3-dimethylo-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "aryl" refers to an aromatic mono- or polycyclic hydrocarbon substituent having the indicated number of carbon atoms. Examples of aryl substituents include -phenyl, -tolyl, -xylyl, -naphthyl, -2,4,6-trimethylphenyl, -2-fluorophenyl, -4-fluorophenyl, -2,4,6-trifluorophenyl, -2,6-difluorophenyl, -4-nitrophenyl and the like.

The term "aralkyl" refers to an alkyl substituent as defined above substituted with at least one aryl as defined above. Examples of aralkyl substituents include -benzyl, -diphenylomethyl, -triphenylomethyl and the like.

The term "heteroaryl" refers to an aromatic mono- or polycyclic hydrocarbon substituent having the indicated number of carbon atoms, in which at least one carbon atom is substituted by a heteroatom selected from O, N and S atoms. Examples of heteroaryl substituents include -furyl, -thienyl, -imidazolyl, -oxazolyl, -thiazolyl, -isoxazolyl, -triazolyl, -oxadiazolyl, -thiadiazolyl, -tetrazolyl, -pyridyl, -pyrimidyl, -triazinyl, -indolyl, -benzo[b]furyl, -benzo[b]thienyl, -indazolyl, -benzoimidazolyl, azaindolyl, -quinolyl, -isoquinolyl, -carbazolyl and the like.

Examples of heterocyclic substituents include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl and the like.

The term "neutral ligand" refers to a non-charged substituent capable of coordinating with a metallic centre (the ruthenium atom). Examples of such ligands may include: amines, phosphines and oxides thereof, alkyl and aryl phosphites and phosphates, arsines and oxides thereof, ethers, alkyl and aryl sulphides, coordinated hydrocarbons, alkyl and aryl halides.

The term "anionic ligand" refers to a substituent capable of coordinating with a metallic centre (the ruthenium atom) with a charge capable of partially or completely compensating the charge of the metallic centre. Examples of such ligands may include fluoride, chloride, bromide, iodide, cyanide, cyanate and thiocyanate anions, carboxylic acid anions, alcohol anions, phenolic anions, thiol and thiophenol anions, delocalized charge hydrocarbon anions (e.g. cyclopentadiene), (organo)sulphuric and (organo)phosphoric acid anions and esters thereof (such as, for example, alkylsulphonic and aryl sulphonic acid anions, alkylphosphoric and arylphosphoric acid anions, sulphuric acid alkyl and aryl ester anions, phosphoric acid alkyl and aryl ester anions, alkylphosphoric and arylphosphoric alkyl and aryl ester anions). Optionally, the anionic ligand may have interconnected $L^1$, $L^2$ and $L^3$ groups, such as the catechol anion, the acetylacetone anion, the salicylaldehyde anion. Anionic ligands ($X^1$, $X^2$) and neutral ligands ($L^1$, $L^2$, $L^3$) may be interconnected to form multidentate ligands, such as a bidentate ligand ($X^1$-$X^2$), a tridentate ligand ($X^1$-$X^2$-$L^1$), a tetradentate ligand ($X^1$-$X^2$-$L^1$-$L^2$), a bidentate ligand ($X^1$-$L^1$), a tridentate ligand ($X^1$-$L^1$-$L^2$), a tetradentate ligand ($X^1$-$L^1$-$L^2$-$L^3$), a bidentate ligand ($L^1$-$L^2$), a tridentate ligand ($L^1$-$L^2$-$L^3$). Examples of such ligands include catechol anion, acetylacetone anion and salicylaldehyde anion.

The term "heteroatom" refers to an atom selected from the group of oxygen, sulphur, nitrogen, phosphorus and the like.

The project is co-financed by the European Union from the European Regional Development Fund under the Operational Programme intelligent Development 2014-2020, based on the contract for co-financing no, POIR.01.01.01-00-0795/17-00.

EMBODIMENTS OF THE INVENTION

The following examples are provided solely for the purpose of illustrating the invention and for clarifying the individual aspects thereof, and not with the intention to limit it, and should not be considered to be equivalent to the total scope thereof as defined in the appended claims. In the examples below, unless otherwise indicated, standard materials and methods were employed as used in the art or it was proceeded according to the manufacturer's recommendations for particular reagents and methods.

The effects of (pre)catalysts 1 according to the invention were compared with (pre)catalysts 12a, 12i, 12j, C1-C5, whose structures are illustrated below:

12a
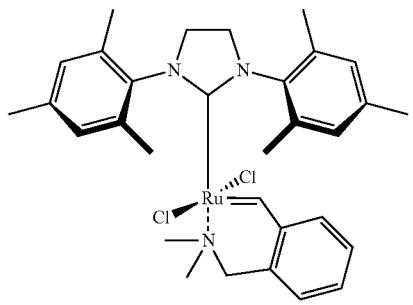

12i
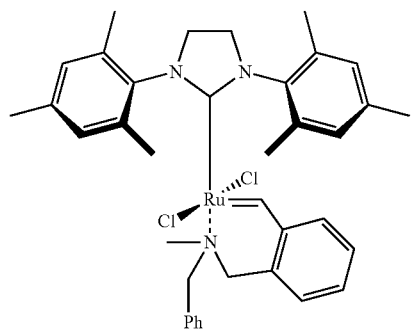

12j
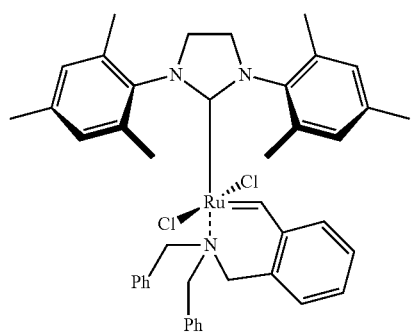

C1
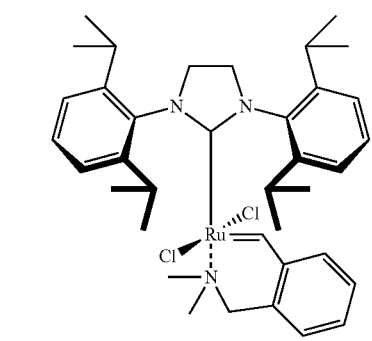

C2
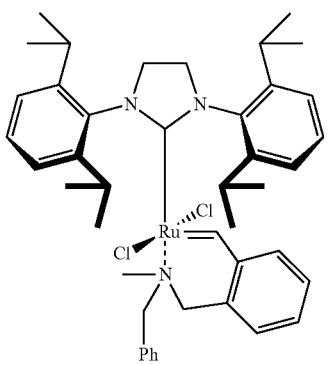

C3
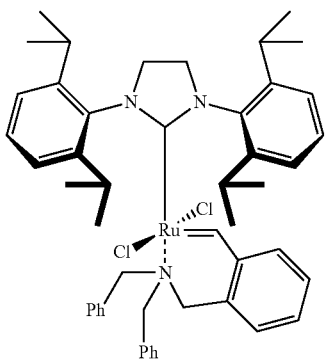

C4
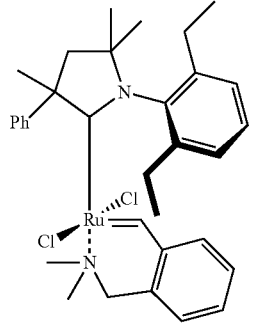

C5
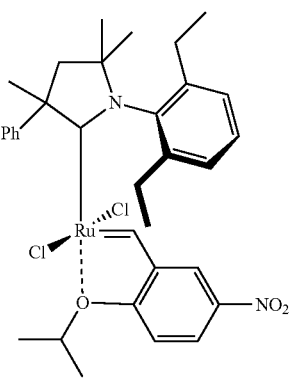

Diethyl malonate (S1), ethyl undecanoate (S2), acrylonitrile and methyl stearate are commercially available compounds. S1 and S2 were distilled under reduced pressure and stored over activated alumina. Acrylonitrile was dried using 4 Å molecular sieves and deoxygenated under argon. All reactions were conducted under argon. Toluene was washed with citric acid, water, dried using 4 Å molecular sieves and deoxygenated under argon.

The composition of reaction mixtures was tested by gas chromatography using a PerkinElmer Clarus 680 GC equipped with the GL Sciences InertCap® 5MS/NP capillary column.

The individual components of reaction mixtures were identified by comparing retention times with commercial standards or standards isolated from reaction mixtures for which the structure was confirmed by NMR.

EXAMPLE I

Reaction for Obtaining the 1a (Pre)Catalyst

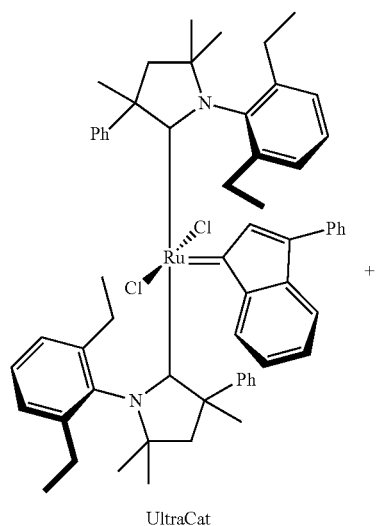

UltraCat

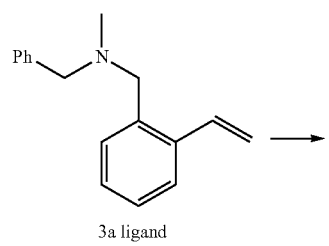

3a ligand

To UltraCat complex (2.002 g, 2.0 mmol, 1 molar eq.) dry deoxygenated toluene (20 ml) and 3a benzylidene ligand (0.475 g, 2.00 mmol, 1.0 molar eq.) were added under argon. The whole was stirred for 10 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1a (pre) catalyst (0.875 g, 61%).

$^1$H NMR (CD$_2$Cl$_2$, 600 MHz): δ=18.55 (s, 1H), 8.59-8.45 (m, 2H), 7.65-7.22 (m, 10H), 7.20-6.80 (m, 4H), 6.51-6.39 (m, 1H), 4.10-3.50 (m, 1H), 3.50-2.90 (br, 2H), 2.85-1.75 (m, 7H), 1.47 (s, 3H), 1.40-0.95 (m, 10H), 0.95-0.50 (m, 5H).

$^{13}$C NMR (CD$_2$Cl$_2$, 150 MHz): δ=318.0, 267.7, 148.3, 148.2, 147.6, 143.5, 143.3, 138.2, 134.4 (2C), 132.8 (2C), 131.5, 131.4, 130.4 (2C), 129.9, 129.8, 129.2, 128.5 (2C), 128.4 (3C), 128.3, 127.6 (3C), 127.5, 126.9, 79.0, 65.5 (2C), 46.6, 32.4, 31.4, 30.4, 29.6, 27.3, 25.9, 24.4, 23.3, 14.8, 14.5, 14.4.

HRMS: ESI was calculated for C$_{41}$H$_{49}$N$_3$ClRu [M-Cl+CH$_3$CN]$^+$: 720.2661; found: 720.2673.

EXAMPLE II

Reaction for Obtaining the 1b (Pre)Catalyst

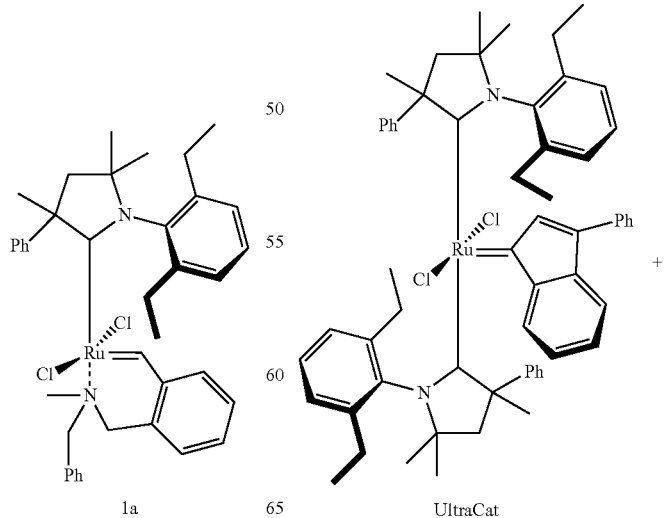

1a      UltraCat

-continued

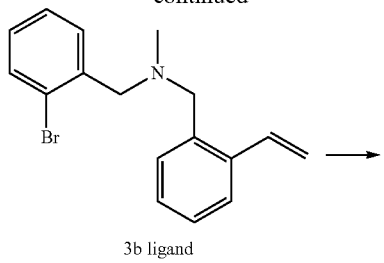

3b ligand

1b

To UltraCat complex (2.002 g, 2.0 mmol, 1 molar eq.) dry deoxygenated toluene (20 ml) and 3b benzylidene ligand (0.632 g, 2.00 mmol, 1.0 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess isopropanol was added. The methylene chloride was slowly removed under reduced pressure. The resulting precipitate was filtered off and washed with cold isopropanol to give a green crystalline solid—1b (pre)catalyst (1.041 g, 66%).

$^1$H NMR (CD$_2$Cl$_2$, 600 MHz): δ=([18.56 (s), 18.49 (s)], 1H), 8.53 (dd, J=19.9; 7.8 Hz, 2H), 7.70-6.80 (m, 13H), 6.43 (dd, J=16.5; 7.8 Hz, 1H), 4.50-3.80 (m, 1H), 3.50-0.35 (m, 27H).

$^{13}$C NMR (CD$_2$Cl$_2$, 150 MHz): δ=317.5, 316.5, 267.6, 267.1, 148.2, 147.9, 147.2, 147.1, 143.6, 143.5, 143.3, 138.3, 138.1, 134.9, 134.3 (2C), 134.1, 134.0, 132.8, 132.6, 131.4 (2C), 130.4, 130.3, 130.3, 130.2, 129.8, 129.7, 129.2, 129.1, 128.7, 128.6, 128.4, 128.2 (2C), 128.1, 127.8, 127.7 (2C), 127.6, 127.5 (2C), 127.3, 127.2, 127.0, 126.8, 79.1, 79.0, 65.4, 65.3, 64.7, 60.6, 46.8, 46.4, 31.4 (2C), 30.3, 30.0, 27.4, 27.3, 26.2, 25.8, 25.7, 24.5, 24.3, 14.9, 14.7, 14.5, 14.4.

HRMS: ESI was calculated for C$_{39}$H$_{45}$N$_2$BrClRu [M-Cl]$^+$: 757.1498; found: 757.1469.

EXAMPLE III

Reaction for Obtaining the 1c (Pre)Catalyst

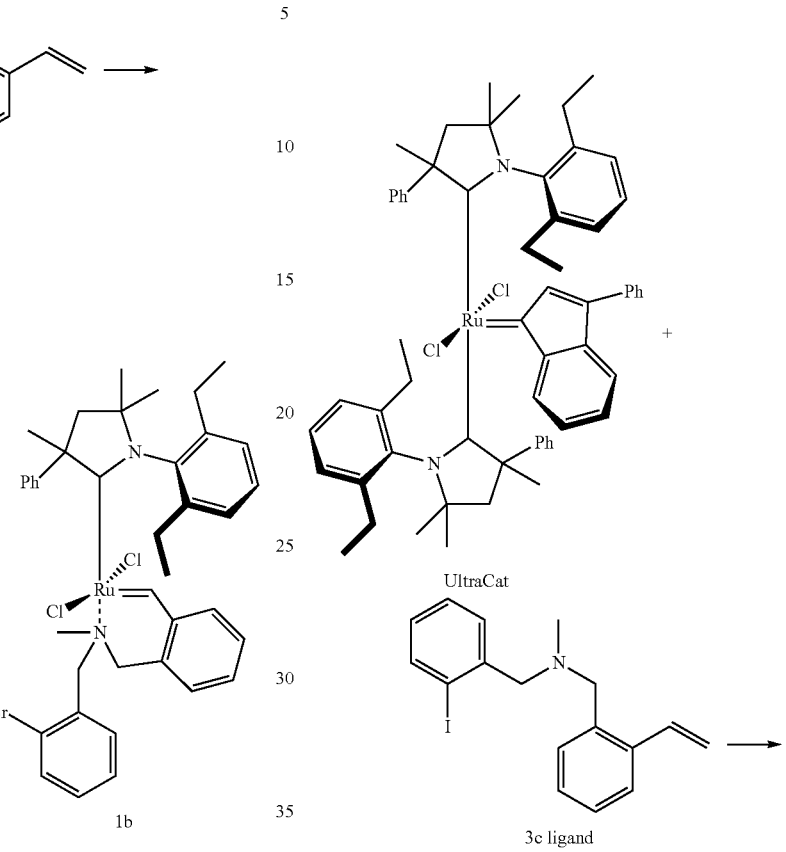

UltraCat 3c ligand

1c

To UltraCat complex (1.001 g, 1.0 mmol, 1 molar eq.) dry deoxygenated toluene (10 ml) and 3c benzylidene ligand (0.363 g, 1.00 mmol, 1.0 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure.

The resulting precipitate was filtered off and washed with cold heptane to give a green crystalline solid—1c (pre)catalyst (0.570 g, 68%).

$^1$H NMR (CD$_2$Cl$_2$, 600 MHz): δ=([18.55 (s), 18.48 (s)], 1H), 8.53 (dd, J=22.7; 7.9 Hz, 2H), 7.92 (d, J=8.3 Hz, 1H), 7.70-6.75 (m, 12H), 6.43 (dd, J=17.7; 7.8 Hz, 1H), 4.80-3.60 (m, 2H), 3.60-1.70 (m, 12H), 1.70-1.10 (m, 10H), 1.10-0.30 (m, 4H).

$^{13}$C NMR (CD$_2$Cl$_2$, 150 MHz): δ=317.6, 316.3, 267.6, 267.0, 148.3, 147.9, 147.0, 143.6, 143.5, 143.4, 143.3, 141.1 (2C), 138.3, 138.1, 136.2, 136.0, 134.3, 133.9, 133.8, 131.4, 131.4, 130.4, 130.4, 130.3, 130.2, 129.8, 129.7, 129.2, 129.1, 128.7, 128.6, 128.4, 128.2, 128.1, 128.0, 127.8, 127.7, 127.6, 127.5 (2C), 127.0, 126.8, 104.6 (2C), 79.1, 79.0, 65.3, 60.7, 46.8, 46.4, 32.4, 31.4, 30.2, 29.6, 27.4, 27.3, 26.2, 25.7, 24.5, 24.3, 23.2, 14.9, 14.6, 14.5, 14.4 (2C).

HRMS: ESI was calculated for C$_{39}$H$_{45}$N$_2$IClRu [M-Cl]$^+$: 805.1359; found: 805.1348.

EXAMPLE IV

Reaction for Obtaining the 1d (Pre)Catalyst

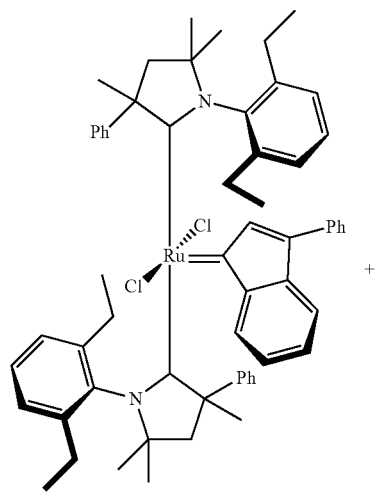

UltraCat

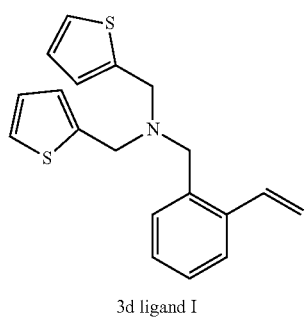

3d ligand I

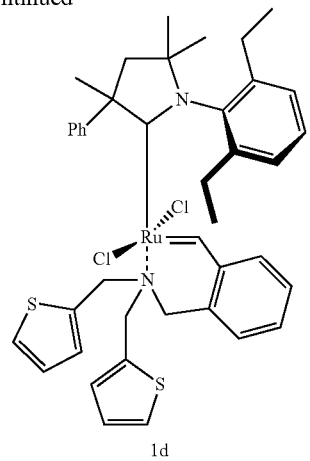

1d

To UltraCat complex (1.001 g, 1.0 mmol, 1 molar eq.) dry deoxygenated toluene (10 ml) and 3d benzylidene ligand (0.325 g, 1.00 mmol, 1.0 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1d (pre)catalyst (0.490 g, 61%).

$^1$H NMR (CD$_2$Cl$_2$, 600 MHz): δ=[19.62 (s), 18.33 (s), 1H], 8.80-5.80 (m, 18H), 4.50-0.20 (m, 27H).

$^{13}$C NMR (CD$_2$Cl$_2$, 150 MHz): δ=317.6, 311.4, 269.6, 267.1, 150.7, 148.3, 146.5, 143.4, 139.8, 138.2, 137.0, 135.1, 134.2, 132.6, 131.3, 130.9, 129.9, 129.6, 129.2, 128.5, 127.7, 127.5, 127.4, 127.0, 79.2, 66.2, 65.2, 58.8, 57.8, 48.0, 32.4, 31.3, 29.6, 27.7, 26.0, 24.5, 23.3, 14.5.

HRMS: ESI was calculated for C$_{41}$H$_{46}$N$_2$ClRuS$_2$ [M-Cl]$^+$: 767.1834; found: 767.1821.

EXAMPLE V

Reaction for Obtaining the 1e (Pre)Catalyst

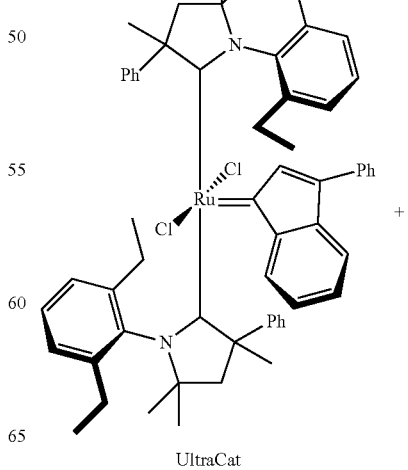

UltraCat

-continued

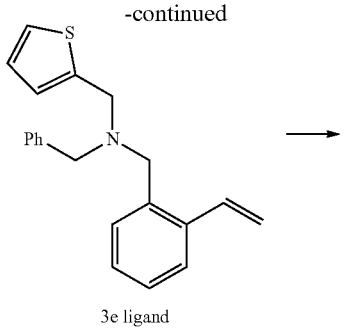

3e ligand

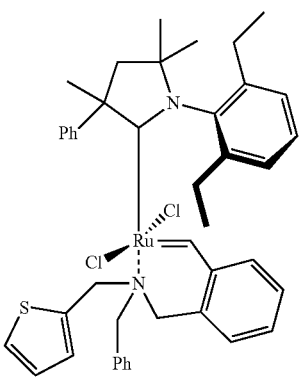

1e

To UltraCat complex (1.001 g, 1.0 mmol, 1 molar eq.) dry deoxygenated toluene (10 ml) and 3e benzylidene ligand (0.319 g, 1.00 mmol, 1.0 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess isopropanol was added. The methylene chloride was slowly removed under reduced pressure. The resulting precipitate was filtered off and washed with cold isopropanol to give a green crystalline solid—1e (pre)catalyst (0.322 g, 40%).

$^1$H NMR (CD$_2$Cl$_2$, 600 MHz): δ=[18.25 (s), 18.21 (s), 1H], 8.75-5.80 (m, 20H), 4.50-0.20 (m, 27H).

$^{13}$C NMR (CD$_2$Cl$_2$, 150 MHz): δ=317.3, 267.6, 148.7, 147.8, 146.9, 146.4, 146.3, 143.4, 143.3, 138.2, 135.8, 132.8 (2C), 131.2 (2C), 130.4, 130.0, 129.9 (2C), 129.5, 129.4 (2C), 129.2, 129.1, 129.0, 128.7 (3C), 128.1 (2C), 127.9, 127.7 (2C), 127.5, 127.4, 127.2, 127.1 (2C), 127.0, 126.9 (2C), 126.5, 120.7, 120.5, 115.1, 114.1, 79.2, 77.9, 70.8, 65.1, 63.3, 58.2, 57.6, 47.5, 32.4, 31.5, 29.6, 29.4, 27.5, 26.3, 25.0, 24.4, 23.26, 14.5.

HRMS: ESI was calculated for C$_{43}$H$_{48}$N$_2$ClRuS [M-Cl]$^+$: 761.2270; found: 761.2253.

EXAMPLE VI

Reaction for Obtaining the 1f (Pre)Catalyst

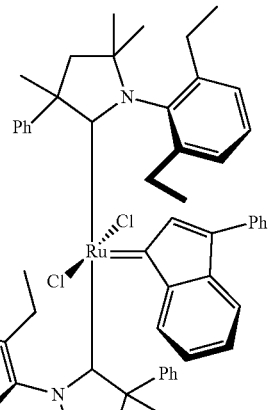

UltraCat

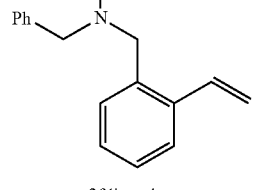

3f ligand

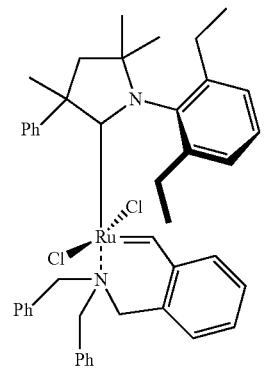

1f

To UltraCat complex (1.502 g, 1.50 mmol, 1 molar eq.) dry deoxygenated toluene (15 ml) and 3f benzylidene ligand (0.564 g, 1.80 mmol, 1.2 molar eq.) were added under argon. The whole was stirred for 10 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1f (pre)catalyst (0.931 g, 78%).

$^1$H NMR (CD$_2$Cl$_2$, 600 MHz): δ=18.07 (s, 1H), 8.52 (br. s, 2H), 7.90-6.20 (m, 19H), 5.91 (d, J=7.7 Hz, 1H), 4.60-0.20 (m, 27H).

$^{13}$C NMR (CD$_2$Cl$_2$, 150 MHz): δ=320.3, 317.4, 269.4, 267.4, 149.0, 146.4, 143.3, 140.1, 136.5, 132.8, 129.9, 129.7, 129.2, 129.1, 128.7, 128.3, 127.7, 127.4 127.0, 126.5, 79.2, 65.0, 64.7, 58.8, 57.6, 47.2, 31.5, 30.2, 29.2, 27.4, 26.6, 25.7, 24.6, 24.1, 18.3, 14.4.

HRMS: ESI was calculated for C$_{45}$H$_{50}$N$_2$ClRu [M-Cl]$^+$: 755.2706; found: 755.2707.

EXAMPLE VII

Reaction for Obtaining the 1g (Pre)Catalyst

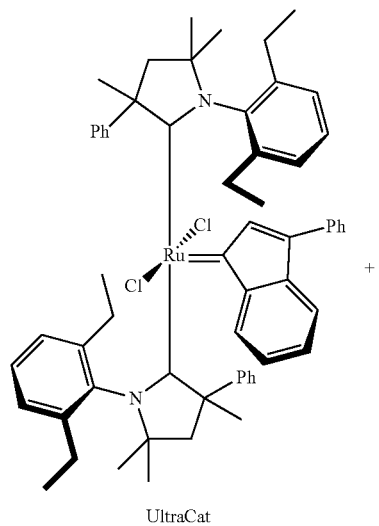

UltraCat

+

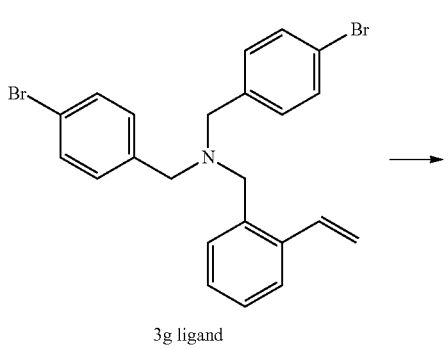

3g ligand

→

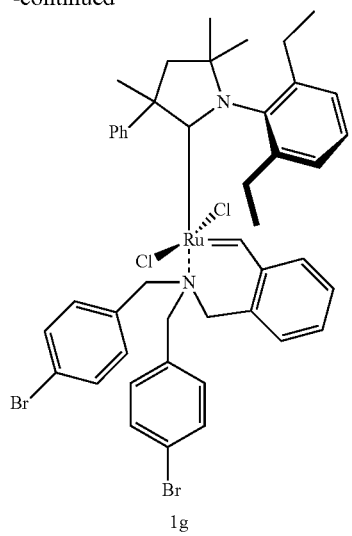

1g

To UltraCat complex (1.001 g, 1.0 mmol, 1 molar eq.) dry deoxygenated toluene (10 ml) and 3g benzylidene ligand (0.707 g, 1.50 mmol, 1.5 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1g (pre) catalyst (0.425 g, 45%).

$^1$H NMR (CD$_2$Cl$_2$, 600 MHz): δ=18.00 (s, 1H), 8.70-8.30 (m, 2H), 7.80-7.05 (m, 13H), 6.90-6.20 (m, 5H), 6.05-5.40 (m, 2H), 5.20-0.20 (m, 25H).

$^{13}$C NMR (CD$_2$Cl$_2$, 150 MHz): δ=319.8, 317.0, 268.6, 266.7, 149.1, 148.6, 146.0, 143.4, 143.0, 138.1, 136.2, 134.6, 132.2, 132.0, 131.9, 131.8, 131.5, 130.4, 130.4, 130.2, 129.9, 129.6, 129.4, 129.2, 128.9, 128.3, 127.8, 127.4, 127.0, 126.5, 123.0, 122.0, 79.3, 65.0, 64.8, 64.6, 64.4, 59.2, 58.7, 58.6, 56.6, 56.2, 47.4, 47.0, 32.4, 31.8, 31.3, 30.4, 29.6, 29.1, 28.9, 28.4, 27.6, 27.4, 27.2, 26.6, 25.4, 24.7, 24.0, 23.9, 23.3, 15.2, 14.8, 14.5, 14.2.

HRMS: ESI was calculated for C$_{45}$H$_{49}$Br$_2$N$_2$Ru [M-2Cl+H]$^+$: 877.1305; found: 877.1319.

EXAMPLE VIII

Reaction for Obtaining the 1h (Pre)Catalyst

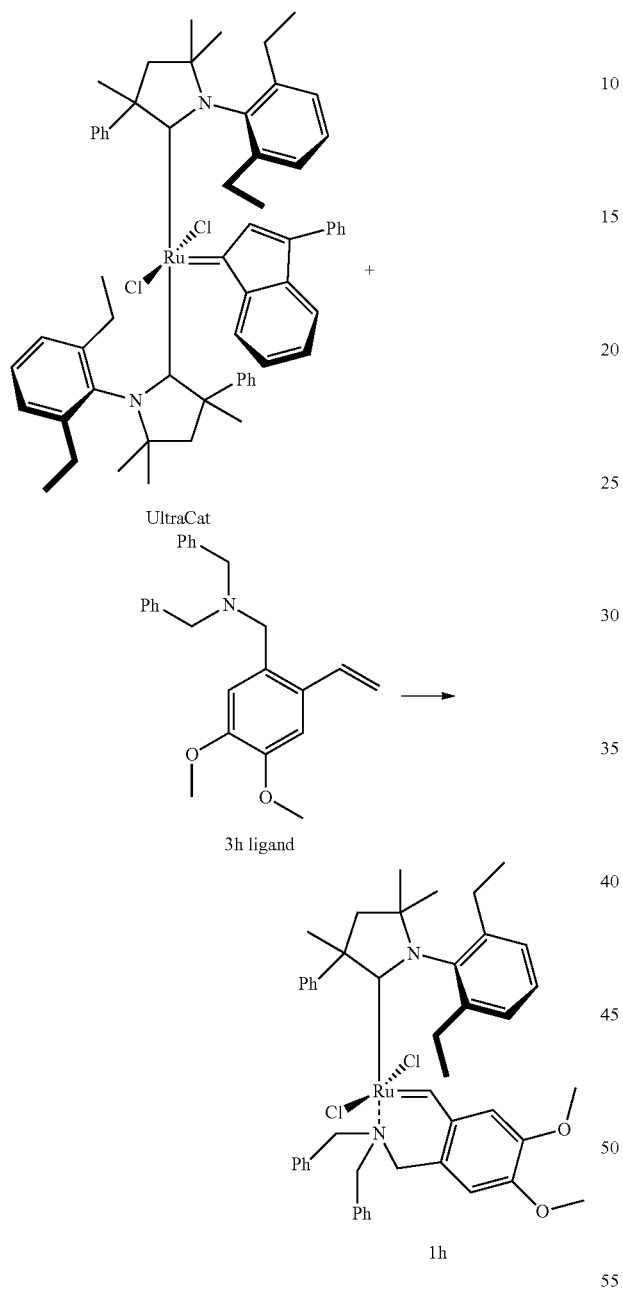

To UltraCat complex (2.002 g, 2.00 mmol, 1 molar eq.) dry deoxygenated toluene (20 ml) and 3h benzylidene ligand (0.896 g, 2.40 mmol, 1.2 molar eq.) were added under argon. The whole was stirred for 20 minutes at 80° C. The mixture was cooled to room temperature and most of the toluene was evaporated. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1h (pre) catalyst (0.450 g, 26%).

$^1$H NMR (CD$_2$Cl$_2$, 600 MHz): δ=17.76 (s, 1H), 8.70-8.30 (m, 2H), 7.70-7.00 (m, 14H), 6.95-6.15 (m, 4H), 4.50-0.40 (m, 33H).

$^{13}$C NMR (CD$_2$Cl$_2$, 150 MHz): δ=316.9, 313.9, 270.3, 268.4, 149.8, 149.0, 148.7, 146.8, 143.9, 140.1, 132.8, 130.6, 130.0, 129.3, 128.7, 128.6, 128.0, 127.6, 127.4, 127.3, 127.2, 114.1, 113.3, 112.9, 111.8, 111.0, 110.3, 79.0, 65.1, 58.5, 56.4, 56.2, 47.3, 46.8, 32.4, 31.7, 31.3, 30.6, 29.6, 29.4, 27.6, 27.2, 26.6, 25.5, 24.8, 24.0, 23.2, 15.2, 14.4.

HRMS: ESI was calculated for C$_{49}$H$_{57}$N$_3$ClO$_2$Ru [M-Cl+CH$_3$CN]$^+$: 856.3188; found: 856.3181.

EXAMPLE IX

Reaction for Obtaining the 1i (Pre)Catalyst

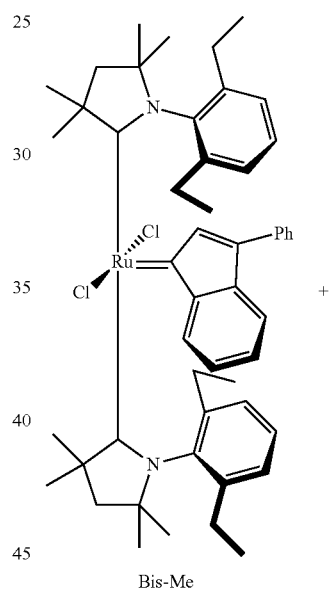

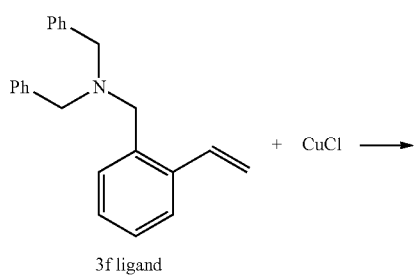

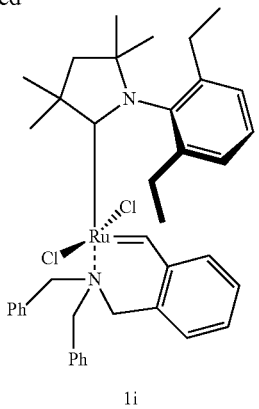

1i

To Bis-Me complex (1.316 g, 1.50 mmol, 1 molar eq.) dry deoxygenated toluene (15 ml), 3f benzylidene ligand (0.564 g, 1.80 mmol, 1.2 molar eq.) and CuCl (0.163 g, 1.65 mmol, 1.1 molar eq.) were added under argon. The whole was stirred for 10 minutes at 70° C. The mixture was cooled to room temperature and evaporated to dryness. The residue was dissolved in ethyl acetate and filtered through a pad of Celite and evaporated to dryness. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1i (pre)catalyst (0.620 g, 57%).

$^1$H NMR (CD$_2$Cl$_2$, 600 MHz): δ=18.36 (s, 1H), 7.55 (t, J=7.7 Hz, 1H), 7.46-7.30 (m, 4H), 7.29-7.02 (m, 9H), 6.95 (td, J=7.5; 1.2 Hz, 1H), 6.85 (dd, J=7.5; 1.3 Hz, 1H), 6.24 (dd, J=7.8; 1.4 Hz, 1H), 4.30-3.70 (m, 4H), 2.90-2.20 (m, 4H), 2.20-1.80 (m, 8H), 1.34-1.16 (m, 8H), 1.10-0.50 (m, 6H).

$^{13}$C NMR (CD$_2$Cl$_2$, 150 MHz): δ=315.6, 315.4, 315.2, 269.9, 148.9, 143.3, 138.4, 135.4, 134.9, 132.7, 130.9, 129.3, 129.0, 128.3, 128.2, 127.6, 127.3, 127.1, 79.8, 59.7, 56.9, 52.7, 31.0, 29.0, 25.1, 14.7.

HRMS: ESI was calculated for C$_{40}$H$_{49}$N$_2$Cl$_2$Ru [M+H]$^+$: 729.2316; found: 729.2307.

EXAMPLE X

Reaction for Obtaining the 1j (Pre)Catalyst

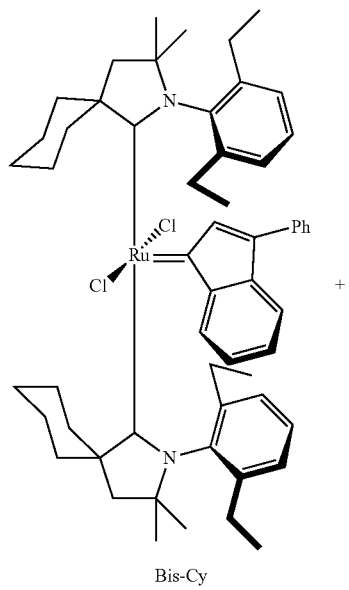

Bis-Cy

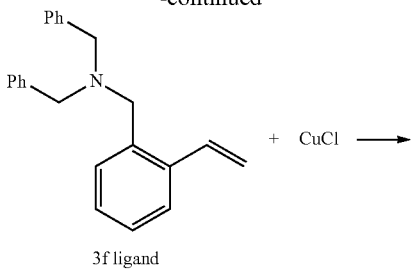

3f ligand

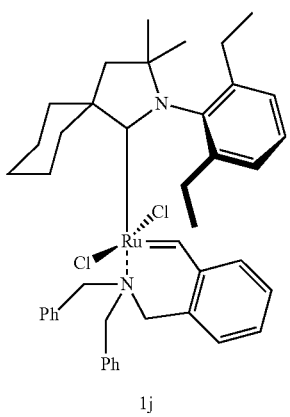

1j

To Bis-Cy complex (1.100 g, 1.15 mmol, 1 molar eq.) dry deoxygenated toluene (15 ml), 3f benzylidene ligand (0.396 g, 1.26 mmol, 1.1 molar eq.) and CuCl (0.171 g, 1.72 mmol, 1.5 molar eq.) were added under argon. The whole was stirred for 10 minutes at 70° C. The mixture was cooled to room temperature and evaporated to dryness. The residue was dissolved in ethyl acetate and filtered through a pad of Celite and evaporated to dryness. The crude product was isolated by column chromatography on silica gel (eluent: ethyl acetate/cyclohexane 2:98→1:9). The green fraction was collected and concentrated to dryness. The residue was dissolved in methylene chloride and excess heptane was added. The methylene chloride was slowly removed under reduced pressure. The resulting precipitate was filtered off and washed with cold heptane to give a green crystalline solid—1j (pre)catalyst (0.585 g, 66%).

$^1$H NMR (CD$_2$Cl$_2$, 600 MHz): δ=18.48 (s, 1H), 8.00-6.40 (m, 16H), 6.28-6.23 (m, 1H), 4.60-1.70 (br m, 17H), 1.56-1.40 (m, 4H), 1.38-1.10 (m, 10H), 0.89 (t, J=7.2 Hz, 3H).

$^{13}$C NMR (CD$_2$Cl$_2$, 150 MHz): δ=316.0, 269.7, 149.0, 143.3, 138.3, 135.3, 134.9, 132.6, 131.0, 129.4, 129.0, 128.2, 127.7, 127.4, 127.1, 79.7, 63.0, 60.0, 45.0, 36.6, 34.7, 29.4, 26.0, 25.2, 23.6, 22.9, 14.7, 14.4.

HRMS: ESI was calculated for C$_{43}$H$_{52}$N$_2$ClRu [M-Cl]$^+$: 733.2863; found: 733.2850.

EXAMPLE XI

Obtaining the 3a Ligand

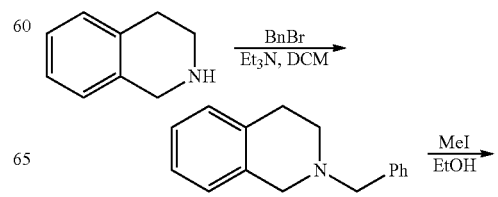

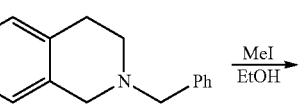

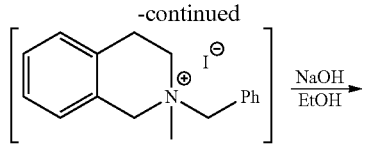

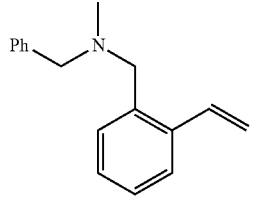

3a ligand

To a solution of 1,2,3,4-tetrahydroisoquinoline (26.600 g, 200.0 mmol, 2 molar eq.) and triethylamine (10.120 g, 100.0 mmol, 1 molar eq.) in methylene chloride (500 ml) cooled to the temperature of 0° C., benzyl bromide (17.100 g, 100.0 mmol, 1 molar eq.) was added dropwise over 10 minutes. The mixture was slowly heated to room temperature and stirred overnight, then washed with water and dried over $Na_2SO_4$. The mixture was then filtered, concentrated and distilled under reduced pressure. The product was collected in a fraction with the boiling point of 126-132° C. at a pressure of $1.1 \times 10^{-2}$ mbar (colourless oil, 18.470 g, 83%).

$^1$H NMR (CDCl$_3$, 600 MHz): δ=7.49-7.45 (m, 2H), 7.43-7.38 (m, 2H), 7.36-7.32 (m, 1H), 7.21-7.14 (m, 3H), 7.06-7.03 (m, 1H), 3.76 (s, 2H), 3.71 (s, 2H), 2.97 (t, J=5.9 Hz, 2H), 2.82 (t, J=5.9 Hz, 2H).

$^{13}$C NMR (CDCl$_3$, 150 MHz): δ=138.4, 134.9, 134.3, 129.0, 128.6, 128.2, 127.0, 126.5, 126.0, 125.5, 62.7, 56.1, 50.6, 29.3.

HRMS: ESI was calculated for $C_{43}H_{52}N_2ClRu$ [M-Cl]$^+$: 224.1434; found: 224.1441.

To the amine obtained in the preceding step (12.946 g, 58.0 mmol, 1 molar eq.) in ethanol (96%, 150 ml), methyl iodide (16.460 g, 116.0 mmol, 2 molar eq.) was added. The whole was stirred at the temperature of 35° C. overnight, and the excess of methyl iodide was evaporated under reduced pressure. NaOH (3.480 g, 87.0 mmol, 1.5 molar eq.) was then added. The mixture was heated while boiling with vigorous stirring under reflux overnight, then cooled and evaporated to dryness. The residue was dissolved in methylene chloride, washed with water and dried over $Na_2SO_4$, then filtered and evaporated to dryness. The crude product was filtered through a thin layer of silica gel (eluent: ethyl acetate/cyclohexane 5:95) and then concentrated to dryness to obtain a colourless oil—the 3a ligand (12.711 g, 92%).

$^1$H NMR (CDCl$_3$, 600 MHz): δ=7.53 (dd, J=7.5; 1.6 Hz, 1H), 7.35-7.27 (m, 5H), 7.26-7.19 (m, 3H), 7.17 (dd, J=17.5; 10.9 Hz, 1H), 5.65 (dd, J=17.6; 1.5 Hz, 1H), 5.26 (dd, J=11.0; 1.5 Hz, 1H), 3.55 (s, 2H), 3.51 (s, 2H), 2.14 (s, 3H).

$^{13}$C NMR (CDCl$_3$, 150 MHz): δ=139.4, 137.7, 136.2, 134.9, 130.4, 129.0, 128.1, 127.3, 126.9, 125.6, 114.8, 62.1, 60.0, 42.0.

HRMS: ESI was calculated for $C_{17}H_{20}N$ [M+H]$^+$: 238.1590; found: 238.1596.

EXAMPLE XII

Obtaining the 3b Ligand

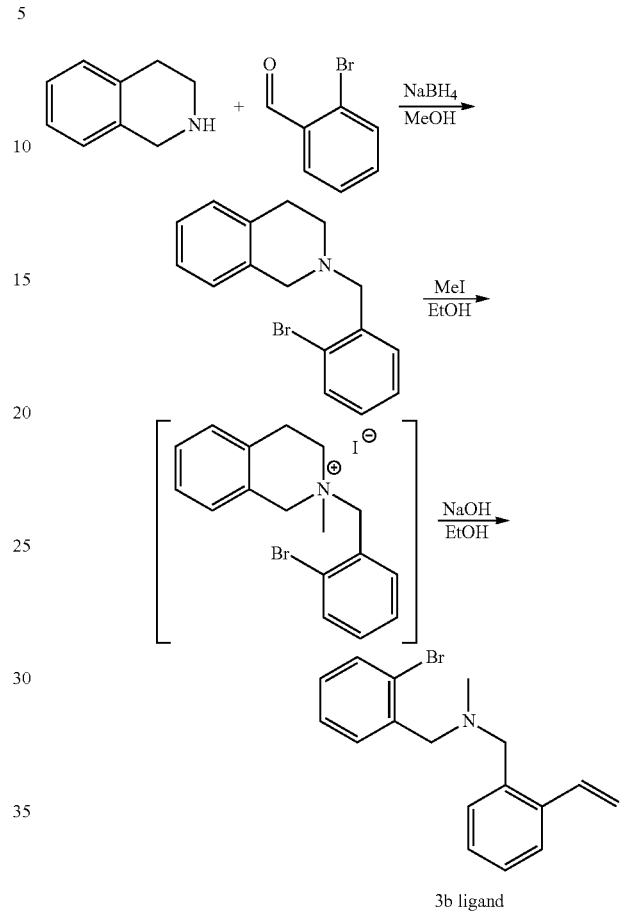

3b ligand

Molecular sieves (3 Å, 3.6 g) were added to a solution of 1,2,3,4-tetrahydroisoquinoline (3.600 g, 27.0 mmol, 1 molar eq.) and 2-bromobenzaldehyde (5.000 g, 27.0 mmol, 1 molar eq.) in methanol (70 ml). The mixture was heated under reflux for 4 hours. After cooling, the mixture was filtered and the solution was placed in a flask fitted with a reflux condenser. Then, NaBH$_4$ (2.045 g, 54.0 mmol, 2 molar eq.) was added portionwise to the mixture with vigorous stirring and left overnight at room temperature. 100 ml of water was added to the mixture, methanol was evaporated and extraction was performed using methylene chloride (3×50 ml). The combined organic extracts were washed with water, dried over $Na_2SO_4$ and evaporated to dryness. The crude product was purified by column chromatography on silica gel (eluent: ethyl acetate/cyclohexane→5:95). The fraction containing the product was evaporated to dryness to obtain a slightly yellow oil (3.673 g, 45%).

$^1$H NMR (CDCl$_3$, 600 MHz): δ=7.62-7.55 (m, 2H), 7.31 (td, J=7.4; 1.2 Hz, 1H), 7.18-7.09 (m, 4H), 7.05-6.98 (m, 1H), 3.81 (s, 2H), 3.74 (s, 2H), 2.95 (t, J=5.9 Hz, 2H), 2.84 (t, J=5.9 Hz, 2H).

$^{13}$C NMR (CDCl$_3$, 150 MHz): δ=137.7, 134.8, 134.3, 132.7, 130.6, 128.7, 128.9, 127.3, 126.6, 126.1, 125.6, 124.5, 61.5, 56.0, 50.8, 29.2.

HRMS: ESI was calculated for $C_{16}H_{17}BrN$ [M+H]$^+$: 302.0539; found: 302.0545.

To the solution of the amine obtained in the preceding step (3.673 g, 12.15 mmol, 1 molar eq.) in methylene chloride (35 ml), methyl iodide (3.45 g, 24.31 mmol, 2 molar eq.) was added. The whole was stirred at the temperature of 35° C. overnight, evaporated to dryness, after which ethanol (96%, 35 ml) and NaOH (0.729 g, 18.23 mmol, 1.5 molar eq.) were added. The mixture was heated under reflux with vigorous stirring overnight. The mixture was cooled and evaporated to dryness. The residue was dissolved in methylene chloride, washed with water and dried over $Na_2SO_4$, then filtered and concentrated to dryness. The crude product was filtered through a thin layer of silica gel (eluent: ethyl acetate/cyclohexane 5:95) and then evaporated to dryness to obtain a slightly yellow oil—the 3b ligand (3.459 g, 90%).

$^1$H NMR (CDCl$_3$, 600 MHz): δ=7.52 (dd, J=7.9; 1.3 Hz, 2H), 7.48 (dd, J=7.7; 1.7 Hz, 1H), 7.33 (dd, J=7.3; 1.8 Hz, 1H), 7.28-7.20 (m, 3H), 7.17 (dd, J=17.5; 11.0 Hz, 1H), 7.09 (td, J=7.7; 1.8 Hz, 1H), 5.63 (dd, J=17.5; 1.5 Hz, 1H), 5.25 (dd, J=11.0; 1.5 Hz, 1H), 4.09 (d, J=5.8 Hz, 4H), 2.18 (s, 3H).

$^{13}$C NMR (CDCl$_3$, 150 MHz): δ=138.4, 137.7, 136.0, 134.9, 132.6, 131.0, 130.4, 128.3, 127.4, 127.4, 127.2, 125.6, 124.6, 114.9, 61.1, 60.1, 42.0.

HRMS: ESI was calculated for $C_{17}H_{19}BrN$ [M+H]$^+$: 316.0695; found: 316.0704.

EXAMPLE XIII

Obtaining the 3c Ligand

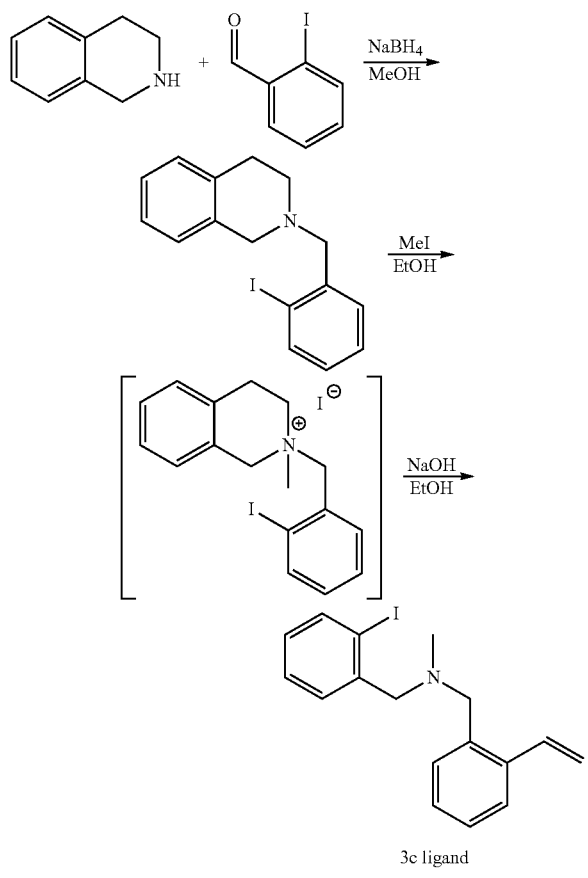

3c ligand

Molecular sieves (3 Å, 1.6 g) were added to a solution of 1,2,3,4-tetrahydroisoquinoline (1.320 g, 9.91 mmol, 1 molar eq.) and 2-iodobenzaldehyde (2.300 g, 9.91 mmol, 1 molar eq.) in methanol (25 ml). The mixture was heated under reflux for 4 hours, and then filtered after cooling. The solution was placed in a flask fitted with a reflux condenser and NaBH$_4$ (0.750 g, 19.83 mmol, 2 molar eq.) was added portionwise with vigorous stirring. The mixture was left overnight at room temperature, then 50 ml of water was added, methanol was evaporated and extraction was performed using methylene chloride (3×20 ml). The combined organic extracts were washed with water and dried over $Na_2SO_4$. This was evaporated to dryness, and the crude product was purified by column chromatography on silica gel (eluent: ethyl acetate/cyclohexane 2:98→1:9). The fraction containing the product was evaporated to dryness to obtain a slightly yellow oil (1.18 g, 34%).

$^1$H NMR (CDCl$_3$, 600 MHz): δ=7.86 (dd, J=7.9; 1.2 Hz, 1H), 7.53 (d, J=7.7 Hz, 1H), 7.33 (td, J=7.5; 1.2 Hz, 1H), 7.17-7.09 (m, 3H), 7.03-7.00 (m, 1H), 6.97 (td, J=7.7; 1.8 Hz, 1H), 3.73 (s, 4H), 2.94 (t, J=5.9 Hz, 2H), 2.84 (t, J=5.8 Hz, 2H).

$^{13}$C NMR (CDCl$_3$, 150 MHz): δ=139.4, 134.3, 130.2, 128.7, 128.7, 128.1, 126.5, 126.1, 125.6, 100.5, 66.3, 55.9, 50.7, 29.2.

HRMS: ESI was calculated for $C_{16}H_{17}IN$ [M+H]$^+$: 350.0400; found: 350.0405.

To the solution of the amine obtained in the preceding step (1.181 g, 33.38 mmol, 1 molar eq.) in methylene chloride (10 ml), methyl iodide (0.960 g, 6.76 mmol, 2 molar eq.) was added. The whole was stirred at the temperature of 35° C. overnight, and evaporated to dryness. Ethanol (96%, 10 ml) and NaOH (0.203 g, 5.07 mmol, 1.5 molar eq.) were then added. The mixture was heated while boiling with vigorous stirring under reflux overnight, then cooled and evaporated to dryness. The residue was dissolved in methylene chloride, washed with water and dried over $Na_2SO_4$, then filtered and evaporated to dryness. The crude product was filtered through a thin layer of silica gel (eluent: ethyl acetate/cyclohexane 5:95) and then concentrated to dryness to obtain a slightly yellow oil—the 3c ligand (1.072 g, 87%).

$^1$H NMR (CDCl$_3$, 600 MHz): δ=7.82 (dd, J=7.9; 1.3 Hz, 1H), 7.51 (dd, J=7.3; 1.7 Hz, 1H), 7.44 (dd, J=7.7; 1.7 Hz, 1H), 7.34 (dd, J=7.1; 1.8 Hz, 1H), 7.30 (td, J=7.4; 1.2 Hz, 1H), 7.25-7.20 (m, 2H), 7.15 (dd, J=17.4; 10.9 Hz, 1H), 6.93 (td, J=7.6; 1.7 Hz, 1H), 5.63 (dd, J=17.5; 1.5 Hz, 1H), 5.24 (dd, J=11.0; 1.5 Hz, 1H), 3.62 (s, 2H), 3.58 (s, 2H), 2.17 (s, 3H).

$^{13}$C NMR (CDCl$_3$, 150 MHz): δ=141.3, 139.3, 137.7, 136.0, 134.9, 130.6, 130.6, 130.4, 128.6, 128.0, 127.4, 127.3, 125.6, 114.9, 100.6, 66.0 (2C), 59.9 (2C), 42.0.

HRMS: ESI was calculated for $C_{17}H_{19}IN$ [M+H]$^+$: 364.0557; found: 364.0574.

EXAMPLE XIV

Obtaining the 3d Ligand

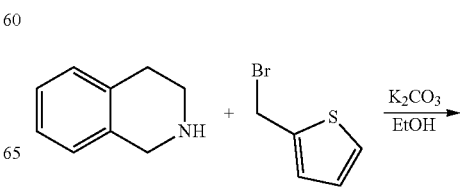

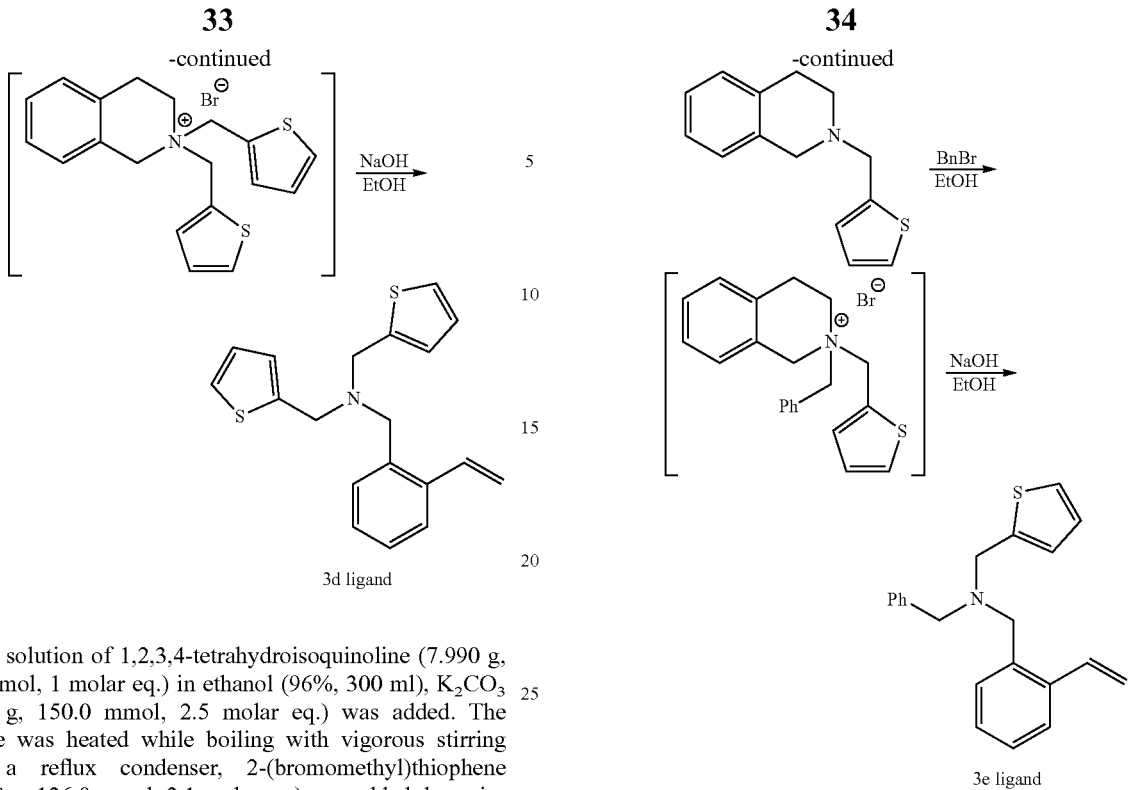

3d ligand

To a solution of 1,2,3,4-tetrahydroisoquinoline (7.990 g, 60.0 mmol, 1 molar eq.) in ethanol (96%, 300 ml), $K_2CO_3$ (20.73 g, 150.0 mmol, 2.5 molar eq.) was added. The mixture was heated while boiling with vigorous stirring using a reflux condenser, 2-(bromomethyl)thiophene (22.310 g, 126.0 mmol, 2.1 molar eq.) was added dropwise over 6 hours. The mixture was heated while boiling over another 6 hours, and then cooled and filtered. NaOH (24.380 g, 150.0 mmol, 2.5 molar eq.) was then added. The mixture was heated under reflux with vigorous stirring over 2 hours. The mixture was then cooled and ethanol was evaporated to obtain yellow oil, which was dissolved in methylene chloride and washed with water. The product was then dried over $Na_2SO_4$, filtered and concentrated to dryness to obtain a slightly yellow oil. The crude product was purified by column chromatography on silica gel (eluent: ethyl acetate/cyclohexane 2:98→5:95). The fraction containing the product was evaporated to dryness to obtain a slightly yellow oil (8.600 g, 44%).

$^1$H NMR (CDCl$_3$, 600 MHz): δ=7.53-7.47 (m, 2H), 7.26-7.20 (m, 4H), 7.14 (dd, J=17.4; 10.9 Hz, 1H), 6.95-6.91 (m, 4H), 5.61 (dd, J=17.4; 1.5 Hz, 1H), 5.27 (dd, J=11.0; 1.5 Hz, 1H), 3.80 (s, 4H), 3.71 (s, 2H).

$^{13}$C NMR (CDCl$_3$, 150 MHz): δ=142.3, 137.7, 135.8, 134.9, 129.8, 127.5, 127.3, 126.4, 126.0, 125.8, 124.9, 115.2, 55.3, 51.6.

HRMS: ESI was calculated for $C_{19}H_{20}NS_2$ [M+H]$^+$: 326.1032; found: 326.1040.

EXAMPLE XV

Obtaining the 3e Ligand

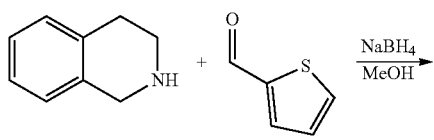

3e ligand

Molecular sieves (3 Å, 11.5 g) were added to a solution of 1,2,3,4-tetrahydroisoquinoline (11.88 g, 89.0 mmol, 1 molar eq.) and thiophen-2-carboxyaldehyde (10.0 g, 89.0 mmol, 1 molar eq.) in methanol (100 ml). The mixture was heated under reflux for 4 hours, and then filtered after cooling. The solution was placed in a flask fitted with a reflux condenser. NaBH$_4$ (3.37 g, 89.0 mmol, 1 molar eq.) was then added portionwise with vigorous stirring and left overnight at room temperature. 200 ml of water was added to the mixture, methanol was evaporated and extraction was performed using methylene chloride (3×100 ml). The combined organic extracts were washed with water, dried over Na$_2$SO$_4$ and evaporated to dryness. The crude product was purified by column chromatography on silica gel (eluent: ethyl acetate/cyclohexane 2:98→1:9). The fraction containing the product was evaporated to dryness to obtain a slightly yellow oil (9.174 g, 45%).

$^1$H NMR (CDCl$_3$, 600 MHz): δ=7.24 (dd, J=4.7; 1.6 Hz, 1H), 7.14-7.07 (m, 3H), 7.00-6.93 (m, 3H), 3.89 (d, J=0.8 Hz, 2H), 3.69 (s, 2H), 2.90 (t, J=5.9 Hz, 2H), 2.78 (t, J=5.9 Hz, 2H).

$^{13}$C NMR (CDCl$_3$, 150 MHz): δ=141.8, 134.6, 134.3, 128.6, 126.6, 126.4, 126.1, 125.9, 125.6, 125.0, 56.8, 55.7, 50.2, 29.1.

HRMS: ESI was calculated for $C_{14}H_{16}NS$ [M+H]$^+$: 230.0998; found: 230.1006.

To the solution the amine obtained in the preceding step (4.326 g, 18.9 mmol, 1 molar eq.) in ethanol (96%, 45 ml), benzyl bromide (3.870 g, 22.6 mmol, 1.2 molar eq.) was added. The mixture was heated while boiling with vigorous stirring under reflux overnight, then cooled and evaporated to dryness, and NaOH (1.13 g, 28.3 mmol, 1.5 molar eq.) was added. The mixture was heated while boiling with vigorous stirring under reflux over 3 hours, then cooled and evaporated to dryness. The residue was dissolved in methylene chloride, washed with water, dried over Na$_2$SO$_4$, filtered and evaporated to dryness. The crude product was purified by column chromatography on silica gel (eluent: ethyl acetate/cyclohexane 2:98→5:95). The fraction containing the product was evaporated to dryness to obtain a slightly yellow oil (4.986 g, 83%).

$^1$H NMR (CDCl$_3$, 600 MHz): δ=7.50-7.44 (m, 2H), 7.41-7.37 (m, 2H), 7.34-7.28 (m, 2H), 7.24-7.19 (m, 4H), 7.07 (dd, J=17.4; 10.9 Hz, 1H), 6.94-6.91 (m, 1H), 6.90-6.88 (m, 1H), 5.59 (dd, J=17.4; 1.6 Hz, 1H), 5.23 (dd, J=10.9; 1.5 Hz, 1H), 3.74 (s, 2H), 3.64 (s, 2H), 3.57 (s, 2H).

$^{13}$C NMR (CDCl$_3$, 150 MHz): δ=142.6, 139.1, 137.7, 136.1, 135.0, 130.0, 128.9, 128.3, 128.2, 127.7, 127.5, 127.4, 127.2, 127.0, 126.3, 125.9, 125.7, 124.8, 114.9, 72.7, 65.7, 57.6, 31.0, 29.0, 55.7, 52.1.

HRMS: ESI was calculated for C$_{21}$H$_{22}$NS [M+H]$^+$: 320.1467; found: 320.1477.

EXAMPLE XVI

Obtaining the 3f Ligand

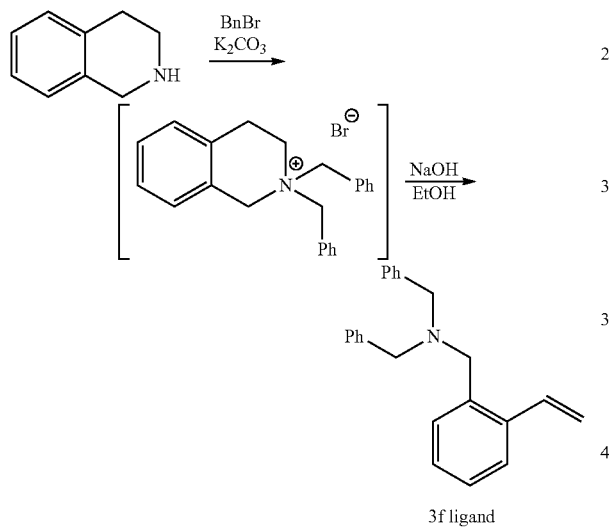

3f ligand

To a solution of 1,2,3,4-tetrahydroisoquinoline (1.332 g, 10.0 mmol, 1 molar eq.) and benzyl bromide (3.590 g, 21.0 mmol, 2.1 molar eq.) in acetonitrile (100 ml), K$_2$CO$_3$ (2.073 g, 15.0 mmol, 1.5 molar eq.) was added. The mixture was heated while boiling with vigorous stirring under reflux over 4 hours, then cooled, filtered and concentrated to dryness. Crude ammonium salt was dissolved in methylene chloride and excess ethyl acetate was added. Methylene chloride was slowly evaporated under reduced pressure. The precipitated product was filtered and washed with ethyl acetate. Ammonium salt was obtained in the form of white crystalline solid (3.880 g, 98%). The ammonium salt obtained in the preceding step was dissolved in ethanol (96%, 50 ml) and NaOH (0.590 g, 14.8 mmol, 1.5 molar eq.) was added. The mixture was heated while boiling with vigorous stirring over 2 hours, then ethanol was cooled and evaporated to obtain yellow oil, which was dissolved in methylene chloride and washed with water. The crude product was then dried over Na$_2$SO$_4$, filtered and evaporated to dryness to obtain a slightly yellow oil (2.605 g, 84%).

$^1$H NMR (CDCl$_3$, 600 MHz): δ=7.56-7.52 (m, 1H), 7.50-7.46 (m, 1H), 7.43-7.39 (m, 4H), 7.38-7.34 (m, 4H), 7.31-7.25 (m, 4H), 7.05 (dd, J=17.4; 10.9 Hz, 1H), 5.64 (dd, J=17.4; 1.6 Hz, 1H), 5.25 (dd, J=10.9; 1.6 Hz, 1H), 3.64 (s, 2H), 3.57 (s, 4H).

$^{13}$C NMR (CDCl$_3$, 150 MHz): δ=137.6, 136.4, 135.1, 130.3, 129.0, 128.1, 127.4, 127.2, 126.9, 125.6, 114.5, 58.2, 56.1, 26.9.

EXAMPLE XVII

Obtaining the 3g Ligand

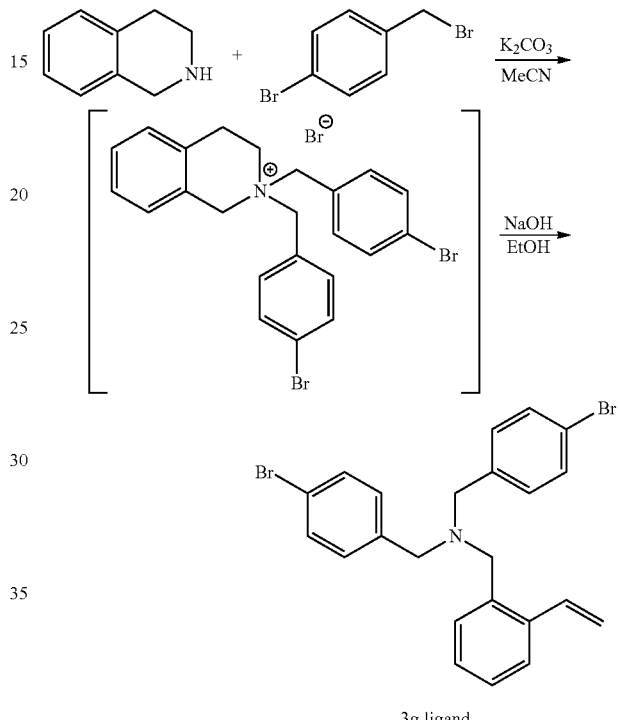

3g ligand

To a solution of 1,2,3,4-tetrahydroisoquinoline (2.660 g, 20.0 mmol, 1 molar eq.) and 4-bromobenzyl bromide (10.500 g, 42.0 mmol, 2.1 molar eq.) in acetonitrile (100 ml), K$_2$CO$_3$ (4.150 g, 30.0 mmol, 1.5 molar eq.) was added. The mixture was heated while boiling with vigorous stirring under reflux over 6 hours, then cooled, filtered and concentrated to dryness, to obtain crude ammonium salt that was used in the next step without purification. The salt was dissolved in ethanol (96%, 100 ml) and NaOH (1.200 g, 30.0 mmol, 1.5 molar eq.) was added. The mixture was heated under reflux with vigorous stirring over 6 hours. Ethanol was cooled and evaporated to obtain yellow oil, which solidifies when stored. The resulting oil was dissolved in methylene chloride, washed with water and excess methanol was added, after which methylene chloride was slowly evaporated under reduced pressure. The precipitated product was filtered and washed with methanol. A product was obtained in the form of white crystalline solid (8.111 g, 86%).

$^1$H NMR (CDCl$_3$, 600 MHz): δ=7.55-7.51 (m, 1H), 7.48-7.43 (m, 4H), 7.40-7.37 (m, 1H), 7.29-7.24 (m, 2H), 7.24-7.20 (m, 4H), 6.96 (dd, J=17.5; 10.9 Hz, 1H), 5.64 (dd, J=17.5; 1.5 Hz, 1H), 5.25 (dd, J=11.0; 1.5 Hz, 1H), 3.59 (s, 2H), 3.46 (s, 4H).

$^{13}$C NMR (CDCl$_3$, 150 MHz): δ=138.2, 137.6, 135.8, 134.9, 131.2, 130.6, 130.2, 127.5, 127.4, 125.8, 120.8, 114.8, 57.4, 56.2.

HRMS: ESI was calculated for $C_{23}H_{22}Br_2N$ [M+H]$^+$: 470.0114; found: 470.0106.

EXAMPLE XVIII

Obtaining the 3h Ligand

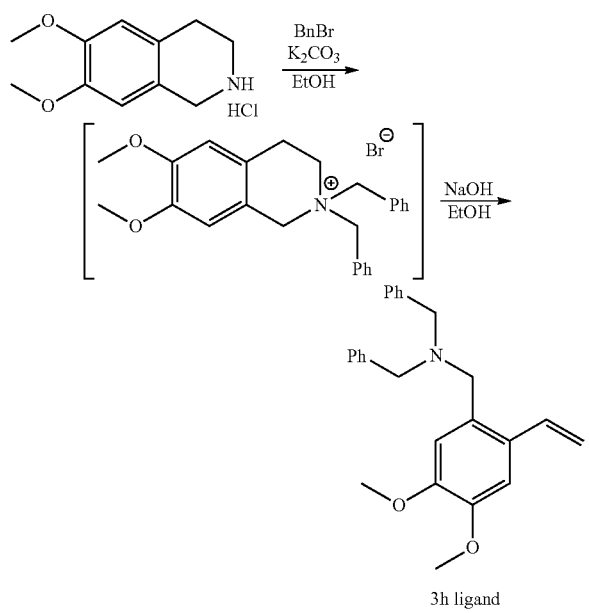

3h ligand

To a solution of 6,7-dimetoxy-1,2,3,4-tetrahydroisoquinoline hydrochloride (11.490 g, 50.0 mmol, 1 molar eq.) and benzyl bromide (21.38 g, 125.0 mmol, 2.5 molar eq.) in ethanol (96%, 250 ml), $K_2CO_3$ (24.190 g, 175.0 mmol, 3.5 molar eq.) was added. The mixture was heated while boiling with vigorous stirring under reflux over 4 hours, then cooled, filtered and concentrated to dryness. Acetone (100 ml) was then added and brought to boil and cooled, then filtered, washed with acetone and dried. Ammonium salt was obtained in the form of white crystalline solid (20.890 g, 92%). This was dissolved in ethanol (96%, 184 ml) and NaOH (4.600 g, 115.0 mmol, 2.5 molar eq.) was added. The mixture was heated while boiling with vigorous stirring over 6 hours, then ethanol was cooled and evaporated to obtain yellow oil, which solidifies when stored. The crude product was dissolved in diethyl ether, washed with water and excess heptane was added. Then diethyl ether was slowly evaporated under reduced pressure. The precipitated product was filtered and washed with heptane. A product was obtained in the form of white crystalline solid (11.580 g, 67%).

$^1$H NMR (CDCl$_3$, 600 MHz): δ=7.41-7.37 (m, 4H), 7.36-7.30 (m, 4H), 7.28-7.22 (m, 2H), 7.05-6.94 (m, 3H), 5.53 (dd, J=17.5; 1.6 Hz, 1H), 5.17 (dd, J=11.0; 1.6 Hz, 1H), 3.94-3.88 (m, 6H), 3.57 (m, 6H).

$^{13}$C NMR (CDCl$_3$, 150 MHz): δ=148.4, 147.9, 139.4, 134.4, 129.8, 129.3, 128.9, 128.1, 126.8, 113.0, 112.6, 108.2, 58.0, 55.9, 55.8, 55.3.

EXAMPLE XIX

RCM Reaction of Diethyl Diallylmalonate (S1)

To the S1 solution (0.240 g, 1.0 mmol) in toluene (10 ml) in the predetermined temperature, the predetermined amount of the appropriate (pre)catalyst in toluene (50 µl) was added in one portion. At adequate intervals, samples were taken of the reaction mixture to which 3 drops of ethyl vinyl ether were added to deactivate the catalyst. The samples were analysed by gas chromatography.

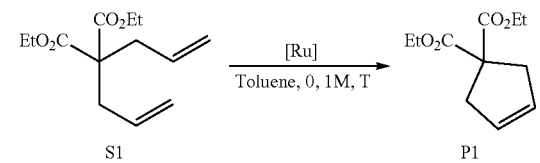

TABLE 1

Experimental results of the RCM reaction of diethyl diallylmalonate S1 at the temperature of 29° C. using 0.1 mol % (pre)catalysts.

| Time [min] | Conversion [%] | | | | | | | | | | | |
|---|---|---|---|---|---|---|---|---|---|---|---|---|
| | 1a | 1b | 1c | 1d | 1e | 1f | 1g | 12a | 12j | C1 | C3 | C4 |
| 2 | — | — | — | 23 | 93 | 98 | 98 | — | 41 | — | 30 | — |
| 5 | — | 8 | 9 | 82 | >99 | >99 | >99 | — | 72 | — | 63 | — |
| 10. | — | 9 | 10. | 99 | — | — | — | — | 91 | — | 90 | — |
| 20 | — | 10. | 13 | >99 | — | — | — | — | 98 | — | 99 | — |
| 30 | — | 11 | 18 | — | — | — | — | — | 99 | — | >99 | — |
| 60 | 4 | 14 | 26 | — | — | — | — | <1 | >99 | <1 | — | <1 |

TABLE 2

Experimental results of the RCM reaction of diethyl diallylmalonate S1 at the temperature of 29° C. using 200 ppm of (pre)catalysts (better differentiation of the fastest (pre)catalysts).

| Time [min] | Conversion [%] | | | | | |
|---|---|---|---|---|---|---|
| | 1d | 1e | 1f | 1g | 1h | C5 |
| 1 | 14 | 24 | 35 | 33 | 24 | 14 |
| 2 | 24 | 48 | 67 | 66 | 47 | 24 |
| 5 | 66 | 93 | >99 | 98 | 98 | 61 |

TABLE 2-continued

Experimental results of the RCM reaction of diethyl diallylmalonate S1 at the temperature of 29° C. using 200 ppm of (pre)catalysts (better differentiation of the fastest (pre)catalysts).

| Time [min] | Conversion [%] | | | | | |
|---|---|---|---|---|---|---|
| | 1d | 1e | 1f | 1g | 1h | C5 |
| 10. | 95 | >99 | — | >99 | 99 | 86 |
| 20 | >99 | — | — | — | >99 | 94 |
| 30 | — | — | — | — | — | 96 |

TABLE 3

Experimental results of the RCM reaction of diethyl diallylmalonate S1 at the temperature of 40° C. using 0.1 mol % (pre)catalysts.

| Time [min] | Conversion [%] | | | | | | | | | | | |
|---|---|---|---|---|---|---|---|---|---|---|---|---|
| | 1a | 1b | 1c | 1d | 1e | 1f | 12a | 12i | 12j | C1 | C2 | C3 | C4 |
| 2 | — | 9 | 9 | >99 | >99 | >99 | — | — | 75 | — | — | 41 | — |
| 5 | — | 11 | 13 | — | — | — | — | — | 95 | — | — | 88 | — |
| 10. | — | 13 | 18 | — | — | — | — | — | >99 | — | — | 99 | — |
| 20 | — | 21 | 32 | — | — | — | — | — | — | — | — | >99 | — |
| 30 | — | 29 | 46 | — | — | — | — | — | — | — | — | — | — |
| 60 | 14 | 45 | 73 | — | — | — | <1 | 16 | — | <1 | 13 | — | <1 |

TABLE 4

Experimental results of the RCM reaction of diethyl diallylmalonate S1 at the temperature of 80° C. using 0.1 mol % (pre)catalysts.

| Time [min] | Conversion [%] | | | | | | | | | |
|---|---|---|---|---|---|---|---|---|---|---|
| | 1a | 1b | 1c | 12a | 12i | 12j | C1 | C2 | C3 | C4 |
| 2 | 30 | 52 | 71 | — | 20 | >99 | — | 13 | >99 | — |
| 5 | 84 | 95 | 99 | — | 51 | — | — | 18 | — | — |
| 10. | 97 | 99 | 99 | — | 77 | — | — | 30 | — | 5 |
| 20 | >99 | >99 | >99 | 13 | 88 | — | 19 | 43 | — | 13 |
| 30 | — | — | — | — | 91 | — | — | 47 | — | 23 |
| 60 | — | — | — | 24 | 94 | — | 33 | 52 | — | 46 |

EXAMPLE XX

CM Reaction of Methyl Acrylate with Ethyl Undecanoate (S2)

To the S2 solution (1.062 g, 1.58 mmol, 1 molar eq.), acrylonitrile (0.655 ml, 10.0 mmol, 2 molar eq.) and methyl stearate (internal standard) in toluene (8.3 ml) at the temperature of 85° C. under argon, a solution of an appropriate (pre)catalyst (100 ppm) in toluene (50 μl) was added, in one portion. The whole was stirred over 1 hour. During the reaction, a stream of argon was passed through the solution. A sample was taken to which 3 drops of ethyl vinyl ether were added to deactivate the catalyst. The sample was analysed by gas chromatography.

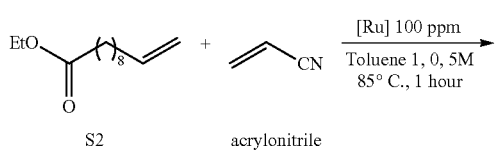

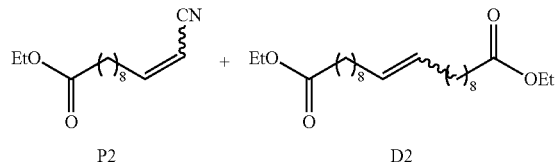

TABLE 5

Experimental results of the CM reaction of acrylonitrile with S2

| (pre)catalyst [Ru] | Conversion [%] | P2 [%] | D2 [%] | Selectivity to P2 [%] |
|---|---|---|---|---|
| 1a | 91 | 84 | 7 | 92 |
| 1b | 97 | 92 | 5 | 95 |
| 1c | 96 | 90 | 6 | 94 |
| 1d | 97 | 92 | 5 | 95 |
| 1e | 94 | 89 | 5 | 95 |
| 1f | 93 | 87 | 6 | 94 |
| 12a | 17 | 16 | 1 | 94 |

TABLE 5-continued

Experimental results of the CM reaction of acrylonitrile with S2

| (pre)catalyst [Ru] | Conversion [%] | P2 [%] | D2 [%] | Selectivity to P2 [%] |
|---|---|---|---|---|
| 12i | 34 | 32 | 2 | 94 |
| 12j | 26 | 24 | 2 | 92 |
| C1 | 5 | 4 | 1 | 80 |
| C2 | 55 | 46 | 9 | 84 |
| C3 | 44 | 37 | 7 | 84 |
| C4 | 21 | 16 | 5 | 76 |

EXAMPLE XXI

Homometathesis Reaction of Ethyl Undecanoate (S2)

To S2 (3.00 g, 14.13 mmol) and methyl stearate (internal standard) at the temperature of 85° C. under argon, a solution of an appropriate (pre)catalyst (30 ppm) in toluene (50 μl) was added, in one portion. The whole was stirred over 1 hour. During the reaction, a stream of argon was passed through the solution. A sample was taken to which 3 drops of ethyl vinyl ether were added to deactivate the catalyst. The sample was analysed by gas chromatography.

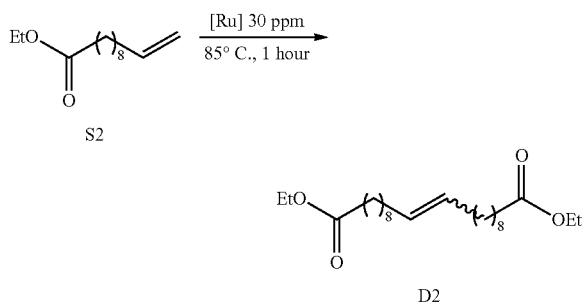

TABLE 6

Experimental results of the homodimerization reaction of S2.

| (pre)catalyst [Ru] | Conversion [%] | D2 [%] | Selectivity to D2 [%] |
|---|---|---|---|
| 1a | 96 | 93 | 97 |
| 1b | 95 | 92 | 97 |
| 1c | 97 | 94 | 97 |
| 1d | 71 | 69 | 97 |
| 1e | 52 | 50 | 96 |
| 1f | 48 | 47 | 97 |
| 12a | 76 | 52 | 69 |
| 12i | 99 | 67 | 68 |
| 12j | 81 | 55 | 68 |
| C1 | 51 | 43 | 84 |
| C2 | 98 | 72 | 74 |
| C3 | 96 | 65 | 68 |
| C4 | 84 | 81 | 97 |
| C5 | 53 | 51 | 97 |

The invention claimed is:

1. A ruthenium complex of formula 1

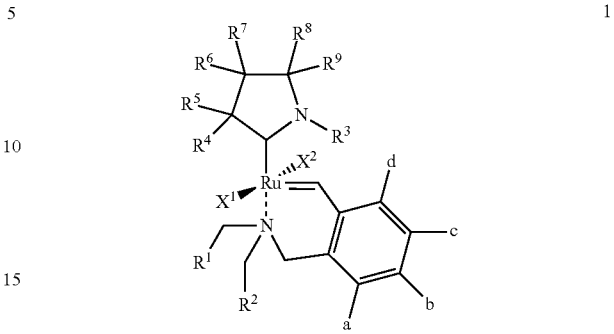

wherein:

$X^1$, $X^2$ are each independently an anionic ligand selected from such as halogen atom, —OR, —SR, —C(C=O)R, where R is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, optionally $C_1$-$C_{12}$ perhalogenalkyl, optionally $C_1$-$C_{12}$ alkoxy, optionally a halogen atom;

$R^1$ is a hydrogen atom or $C_5$-$C_{24}$ aryl, $C_1$-$C_{25}$ alkyl, $C_5$-$C_{25}$ heteroaryl, $C_7$-$C_{24}$ aralkyl, which are optionally substituted by at least one $C_1$-$C_{12}$ alkyl, optionally $C_1$-$C_{12}$ perhalogenalkyl, optionally $C_1$-$C_{12}$ alkoxy, optionally a halogen atom, wherein the alkyl groups may be interconnected to form a ring;

$R^2$ is $C_5$-$C_{24}$ aryl, $C_5$-$C_{25}$ heteroaryl, $C_7$-$C_{24}$ aralkyl, which are optionally substituted by at least one $C_1$-$C_{12}$ alkyl, optionally $C_1$-$C_{12}$ perhalogenalkyl, optionally $C_1$-$C_{12}$ alkoxy, optionally a halogen atom, wherein the alkyl groups may be interconnected to form a ring;

$R^3$ is $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_2$-$C_{12}$ alkoxy or a halogen atom;

$R^4$, $R^5$, $R^6$, $R^7$, $R^8$, $R^9$ are each independently a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_1$-$C_{12}$ alkoxy or a halogen atom, and the $R^4$ and $R^5$ and/or $R^8$ and $R^9$ groups may optionally be interconnected to form a cyclic system $C_4$-$C_{10}$; and a, b, c, d—are each independently a hydrogen atom, a halogen atom, $C_1$-$C_{25}$ alkyl, $C_1$-$C_{25}$ perfluoroalkyl, $C_3$-$C_7$ cycloalkyl, $C_1$-$C_{25}$ alkoxy, $C_5$-$C_{24}$ aryl, $C_7$-$C_{24}$ aralkyl, $C_5$-$C_{25}$ heteroaryl, 3-12-membered heterocycle, wherein the alkyl groups may be interconnected to form a ring; also, each of them can be independently an ether (—OR'), thioether (—SR'), nitro (—NO2), cyano (—CN), amide (—CONR'R"), carboxy and ester (—COOR'), sulfa (—SO2R'), sulfonamide (SO2NR'R"), formyl and ketone (—COR') group, in which groups R' and R" are each $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl.

2. The complex according to claim 1, characterised in that:

$X^1$ and $X^2$ are halogen atoms;

$R^3$ is aryl, which is optionally substituted by at least one $C_1$-$C_{12}$ alkyl, $C_1$-$C_{12}$ perhalogenalkyl, $C_2$-$C_{12}$ alkoxy or a halogen atom;

$R^4$, $R^5$, $R^8$, $R^9$ are each independently a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted by at least one $C_1$-$C_{12}$ alkyl, $C_1$-$C_{12}$ perhalogenalkyl, $C_1$-$C_{12}$ alkoxy or a halogen atom, and the $R^4$ and $R^5$ and/or the $R^8$ and $R^9$, groups may optionally be interconnected to form a cyclic system $C_4$-$C_{10}$;

$R^6$, $R^7$ are hydrogen atoms; and a, b, c, d—are each independently a halogen atom, an ether (—OR'), thioether (—SR'), nitro (—NO2), cyano (—CN), amide (—CONR'R"), carboxy and ester (—COOR'), sulfa (—SO2R'), sulfonamide (—SO2NR'R"), formyl and ketone (—COR') group, in which groups R' and R" are each independently $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl.

3. The complex according to claim 1, characterised in that:

$X^1$ and $X^2$ are halogen atoms;

$R^3$ is aryl, which is optionally substituted by at least one $C_1$-$C_{12}$ alkyl, $C_1$-$C_{12}$ perhalogenalkyl, $C_2$-$C_{12}$ alkoxy or a halogen atom;

$R^4$, $R^5$, $R^8$, $R^9$ are each independently a hydrogen atom, $C_1$-$C_{12}$ alkyl, $C_3$-$C_{12}$ cycloalkyl, $C_5$-$C_{20}$ aryl, which is optionally substituted by at least one $C_1$-$C_{12}$ alkyl, and $R^4$ and $R^5$ and/or the $R^8$ and $R^9$, groups may optionally be interconnected to form a cyclic system $C_4$-$C_{10}$;

$R^6$, $R^7$ are hydrogen atoms; and a, b, c, d—are each independently a halogen atom, an ether (—OR'), nitro (—NO2), amide (—CONR'R"), ester (—COOR'), sulfa (—SO2R'), sulfonamide (—SO2NR'R") group, in which groups R' and R" are each $C_1$-$C_{25}$ alkyl, $C_5$-$C_{24}$ aryl.

4. The complex according to claim 1, characterised in that:

$X^1$ and $X^2$ are chlorine atoms;

$R^3$ is aryl, which is optionally substituted by at least one $C_1$-$C_{12}$ alkyl;

$R^4$, $R^5$ are each independently $C_1$-$C_{12}$ alkyl, $C_5$-$C_{20}$ aryl, which is optionally substituted by at least one $C_1$-$C_{12}$ alkyl, and the $R^4$ and $R^5$ groups may optionally be interconnected to form a cyclic system $C_4$-$C_{10}$;

$R^6$, $R^7$ are hydrogen atoms;

$R^8$, $R^9$ are each independently $C_1$-$C_{12}$ alkyl; and a, b, c, d—are each independently a halogen atom, an ether (—OR') group, in which group R' denotes as follows: $C_1$-$C_{25}$ alkyl.

5. The complex according to claim 1, characterised in that:

$X^1$ and $X^2$ are chlorine atoms;

$R^3$ is aryl, which is optionally substituted by at least one $C_1$-$C_{12}$ alkyl;

$R^4$, $R^5$ are each independently $C_1$-$C_{12}$ alkyl, $C_5$-$C_{20}$ aryl, and the $R^4$ and $R^5$ groups may optionally be interconnected to form a cyclic system $C_4$-$C_{10}$;

$R^6$, $R^7$ are hydrogen atoms;

$R^8$, $R^9$ are each independently methyl groups; and a, b, c, d—are each a hydrogen atom or a metoxy (—OMe) group.

6. The complex according to claim 1 with a structure represented by a structural formula select from formulas 1a-1j:

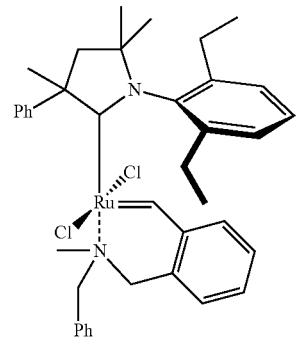

1a

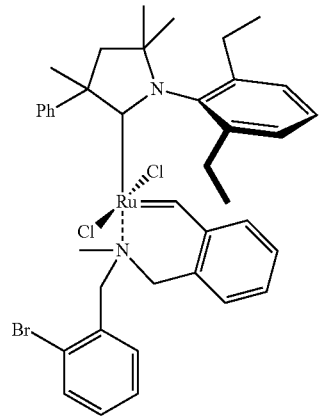

1b

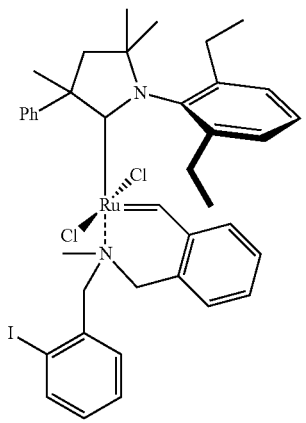

1c

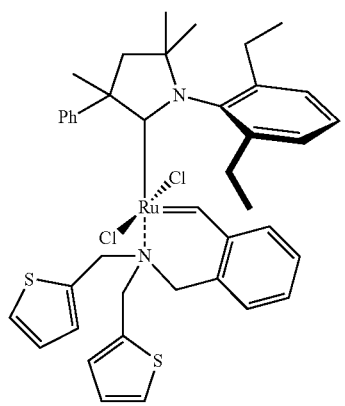

1d

1e 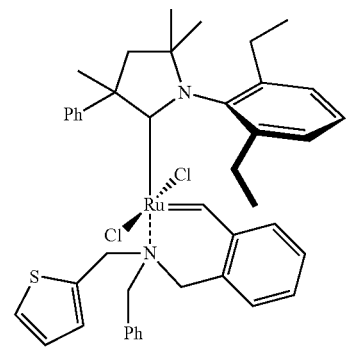

1f 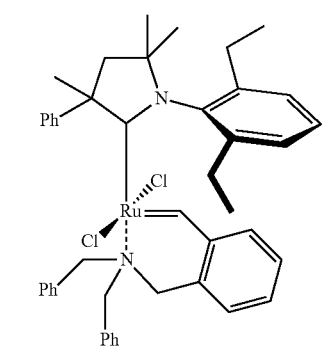

1g 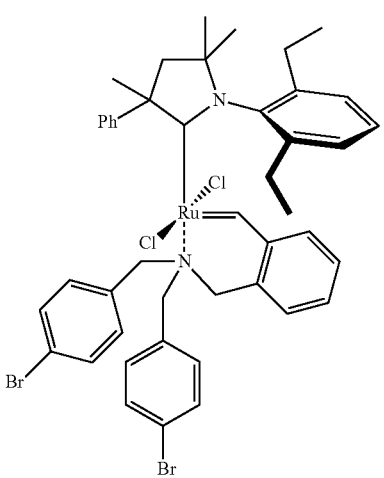

1h 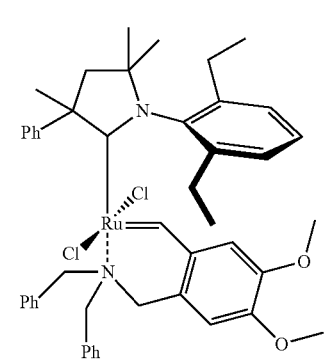

1i 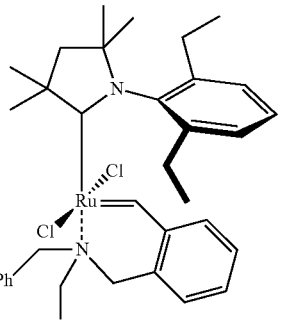

1j 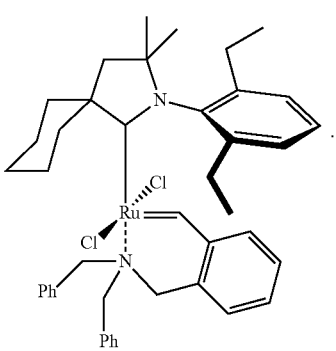

7. A method comprising:
adding the ruthenium complex according to claim 1 as a (pre)catalyst to a solution to produce an olefin metathesis reaction.

8. The method of claim 7, wherein the adding step is accomplished by using the ruthenium complex according to claim 1 as a (pre)catalyst for a ring metathesis reaction (RCM), homometathesis (self-CM), or cross-metathesis, including ethenolysis (CM).

9. The method of claim 7 wherein the adding step is accomplished by using a solution that is an organic solvent such as toluene, benzene, mesitylene, dichloromethane, ethyl acetate, methyl acetate, tertbutyl methyl ether, or cyclopentylmethyl ether.

10. The method of claim 7 wherein the adding step is accomplished by conducting the olefin metathesis reaction at a temperature between O and 150° C.

11. The method of claim 7 wherein the adding step is accomplished by conducting the olefin metathesis reaction at a temperature between 40 and 120° C.

12. The method of claim 7 wherein the adding step accomplished by conducting the olefin metathesis reaction between 1 minute and 24 hours.

13. The method of claim 7 wherein the adding step is accomplished by using the ruthenium complex according to claim 1 in a quantity of no more than 0.1 mol %.

14. The method of claim 13 wherein the using step is accomplish by adding the ruthenium complex according to claim 1 to the reaction mixture as a solid and/or as a solution in an organic solvent.

15. The method of claim 7 wherein the adding step is accomplished by using a solution that is solvent-free.

* * * * *